(12) United States Patent
Travers et al.

(10) Patent No.: US 9,542,527 B2
(45) Date of Patent: *Jan. 10, 2017

(54) COMPOSITIONS AND METHODS FOR NUCLEIC ACID SEQUENCING

(71) Applicant: Pacific Biosciences of California, Inc., Menlo Park, CA (US)

(72) Inventors: Kevin Travers, Menlo Park, CA (US);
Geoff Otto, Brookline, MA (US);
Stephen Turner, Seattle, WA (US);
Cheryl Heiner, La Honda, CA (US);
Congcong Ma, Foster City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/497,067

(22) Filed: Sep. 25, 2014

(65) Prior Publication Data

US 2015/0159196 A1    Jun. 11, 2015

Related U.S. Application Data

(63) Continuation of application No. 13/866,603, filed on Apr. 19, 2013, which is a continuation of application No. 13/403,789, filed on Feb. 23, 2012, now Pat. No. 8,455,193, which is a continuation of application No. 12/413,258, filed on Mar. 27, 2009, now Pat. No. 8,153,375.

(60) Provisional application No. 61/099,696, filed on Sep. 24, 2008, provisional application No. 61/072,160, filed on Mar. 28, 2008.

(51) Int. Cl.
| | | |
|---|---|---|
| *C12P 19/34* | (2006.01) | |
| *C12Q 1/68* | (2006.01) | |
| *C07H 21/02* | (2006.01) | |
| *C07H 21/04* | (2006.01) | |
| *C07H 21/00* | (2006.01) | |
| *G06F 19/22* | (2011.01) | |

(52) U.S. Cl.
CPC ............. *G06F 19/22* (2013.01); *C12Q 1/6806* (2013.01); *C12Q 1/6869* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS

| | | | |
|---|---|---|---|
| 5,001,050 A | 3/1991 | Blanco et al. | |
| 5,162,654 A | 11/1992 | Kostichka et al. | |
| 5,198,543 A | 3/1993 | Blanco et al. | |
| 5,350,686 A | 9/1994 | Jhingah | |
| 5,470,724 A | 11/1995 | Ahern | |
| 5,547,839 A | 8/1996 | Dower et al. | |
| 5,576,204 A | 11/1996 | Blanco et al. | |
| 5,629,468 A | 5/1997 | Schwarz et al. | |
| 5,648,245 A | 7/1997 | Fire et al. | |
| 5,674,683 A | 10/1997 | Kool | |
| 5,674,716 A | 10/1997 | Tabor et al. | |
| 5,714,320 A | 2/1998 | Kool | |
| 5,854,033 A | 12/1998 | Lizardi | |
| 5,948,616 A | 9/1999 | Chao et al. | |
| 6,080,545 A | 6/2000 | Popoff et al. | |
| 6,087,099 A | 7/2000 | Gupte et al. | |
| 6,103,465 A | 8/2000 | Johnston-Dow et al. | |
| 6,143,495 A | 11/2000 | Lizardi et al. | |
| 6,210,891 B1 | 4/2001 | Nyren et al. | |
| 6,210,896 B1 | 4/2001 | Chan | |
| 6,235,502 B1 | 5/2001 | Weissman et al. | |
| 6,235,503 B1 | 5/2001 | Lindemann et al. | |
| 6,251,610 B1 | 6/2001 | Gupte et al. | |
| 6,255,083 B1 | 7/2001 | Williams | |
| 6,261,808 B1 | 7/2001 | Auerbach | |
| 6,287,824 B1 | 9/2001 | Lizardi et al. | |
| 6,291,187 B1 | 9/2001 | Kingsmore et al. | |
| 6,369,038 B1 | 4/2002 | Blumenfeld et al. | |
| 6,451,563 B1 | 9/2002 | Wittig et al. | |
| 6,498,023 B1 | 12/2002 | Abarzua | |
| 6,723,513 B2 | 4/2004 | Lexow | |
| 6,787,308 B2 | 9/2004 | Balasubramanian | |
| 6,849,404 B2 | 2/2005 | Park et al. | |

(Continued)

FOREIGN PATENT DOCUMENTS

| | | |
|---|---|---|
| EP | 1225234 B1 | 11/2007 |
| EP | 1907573 B1 | 1/2010 |

(Continued)

OTHER PUBLICATIONS

Nagai et al., A novel sperm-specific hypomethylation sequence is a demethylation hotspot in human hepatocellular carcinomas. Gene, 237, 15-20, 1999.*
First Exam Report dated Sep. 25, 2014 for related case IN 6817/CHENP/2010.
Figure 1A and 1B of US 2007/0087358 A1 with the examiner's handwritings, Printed on Oct. 5, 2012.
First Exam Report dated Apr. 7, 2015 for related case CA 2719747.
Bashir, A. et al., "Evaluation of paired-end sequencing strategies for detection of genome rearrangements in cancer" Plos CompBiol (2008) 4(4):1-14.
Eid, et al., "Real-time DNA sequencing from single polymerase molecules" Science (2009) 323(5910):133-138.
Harris, T.D. et al., "Single-molecule DNA sequencing of a viral genome" Science (2008) 320:106-109.

(Continued)

*Primary Examiner* — Frank Lu
(74) *Attorney, Agent, or Firm* — Robert H. Reamey

(57) ABSTRACT

Compositions and methods for nucleic acid sequencing include template constructs that comprise double stranded portions in a partially or completely contiguous constructs, to provide for redundant sequence determination through one or both of sequencing sense and antisense strands, and iteratively sequencing the entire construct multiple times. Additional sequence components are also optionally included within such template constructs. Methods are also provided for the use and preparation of these constructs as well as sequencing compositions for their application.

11 Claims, 17 Drawing Sheets

(56) References Cited

U.S. PATENT DOCUMENTS

| | | |
|---|---|---|
| 6,917,726 B2 | 7/2005 | Levene et al. |
| 7,013,054 B2 | 3/2006 | Levene et al. |
| 7,033,764 B2 | 4/2006 | Korlach et al. |
| 7,045,362 B2 | 5/2006 | Hartwich et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Korlach et al. |
| 7,181,122 B1 | 2/2007 | Levene et al. |
| 7,229,799 B2 | 6/2007 | Williams et al. |
| 7,282,337 B1 | 10/2007 | Harris et al. |
| 7,292,742 B2 | 11/2007 | Levene et al. |
| 7,361,466 B2 | 4/2008 | Korlach et al. |
| 7,368,265 B2 | 5/2008 | Brenner et al. |
| 7,416,844 B2 | 8/2008 | Korlach et al. |
| 7,476,503 B2 | 1/2009 | Turner et al. |
| 7,485,424 B2 | 2/2009 | Korlach et al. |
| 7,601,495 B2 | 10/2009 | Chen et al. |
| 7,601,499 B2 | 10/2009 | Berka et al. |
| 7,700,287 B2 | 4/2010 | Chen et al. |
| 7,754,429 B2 | 7/2010 | Rigatti et al. |
| 7,767,400 B2 | 8/2010 | Harris et al. |
| 7,901,889 B2 | 3/2011 | Christians et al. |
| 8,153,375 B2 | 4/2012 | Travers et al. |
| 8,455,193 B2 | 6/2013 | Travers et al. |
| 2001/0030290 A1 | 10/2001 | Stem |
| 2003/0044781 A1 | 3/2003 | Korlach et al. |
| 2003/0096253 A1 | 5/2003 | Nelson et al. |
| 2003/0143550 A1 | 7/2003 | Green et al. |
| 2003/0175729 A1 | 9/2003 | Van Eijk et al. |
| 2003/0190647 A1 | 10/2003 | Odera |
| 2003/0207279 A1 | 11/2003 | Crothers et al. |
| 2003/0213771 A1 | 11/2003 | Ohshita et al. |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0203008 A1 | 10/2004 | Uemori et al. |
| 2004/0224319 A1 | 11/2004 | Sood et al. |
| 2004/0259082 A1 | 12/2004 | Williams |
| 2005/0176035 A1 | 8/2005 | Crothers et al. |
| 2006/0040297 A1* | 2/2006 | Leamon et al. .......... 435/6 |
| 2006/0061754 A1 | 3/2006 | Turner et al. |
| 2006/0063171 A1 | 3/2006 | Akeson et al. |
| 2006/0063264 A1 | 3/2006 | Turner et al. |
| 2006/0292611 A1 | 12/2006 | Berka et al. |
| 2007/0062934 A1 | 3/2007 | King |
| 2007/0087358 A1 | 4/2007 | Ehrlich et al. |
| 2007/0161017 A1 | 7/2007 | Eid et al. |
| 2007/0178482 A1 | 8/2007 | Lezhava et al. |
| 2007/0196832 A1* | 8/2007 | Efcavitch .......... C12Q 1/6827 435/6.14 |
| 2007/0269825 A1 | 11/2007 | Wang et al. |
| 2008/0026393 A1 | 1/2008 | Mindrinos et al. |
| 2008/0233575 A1 | 9/2008 | Harris et al. |
| 2009/0005252 A1 | 1/2009 | Drmanac et al. |
| 2009/0181861 A1 | 7/2009 | Li et al. |
| 2009/0197257 A1 | 8/2009 | Harris |
| 2009/0269771 A1 | 10/2009 | Schroeder |
| 2009/0305248 A1 | 12/2009 | Lander et al. |
| 2010/0121582 A1 | 5/2010 | Pan et al. |
| 2011/0212436 A1 | 9/2011 | Christians et al. |
| 2012/0058468 A1 | 3/2012 | McKeown |

FOREIGN PATENT DOCUMENTS

| | | |
|---|---|---|
| WO | 9106678 A1 | 5/1991 |
| WO | 9416090 A1 | 7/1994 |
| WO | 9627025 A1 | 9/1996 |
| WO | 9905315 A2 | 2/1999 |
| WO | 2002004680 A2 | 1/2002 |
| WO | 2007003017 A1 | 1/2007 |
| WO | 2007010263 A2 | 1/2007 |
| WO | 2007070572 | 6/2007 |
| WO | 2008058282 | 5/2008 |
| WO | 2009124255 A2 | 10/2009 |

OTHER PUBLICATIONS

Hong, Y.S. et al., "Construction of a BAC library and generation of BAC end sequence-tagged connectors for genome sequencing" Mol Genet Genomics (2003) 268:720-728.

Keane, T. et al., "Assessing assemblability of reads from new sequencing platforms" Wellcome Trust Poster, p. 1.

Koonin et al. "Computer-assisted dissection of rolling circle DNA replication" Biosystems (1993) 30(1-3):241-268.

Korbel, J.O. et al. "Paired-end mapping reveals extensive structural variation in the human genome" Science (2007) 318:420-426.

Kuhn et al., "Rolling-circle amplificaiton under topological constraints" Nucl Acids Res (2002) 30(2):574-580.

Levene et al., "Zero-mode waveguides for single-molecule analysis at high concentrations" Science (2003) 299(5607):682-686.

Matray, T.J. et al. "A specific partner for abasic damage in DNA" Nature (1999) 399:704-708.

Myers, G. "Whole-genome DNA sequencing" IEEE (May-Jun. 1999) pp. 33-43.

Novick "Contrasting lifestyles of rolling-circle phages and plasmids" Trends Biochem Sci (1998) 23(11):434-438.

Reifenberger, J. et al., Advances in Genome Biol and Tech (AGBT) (2009) Abstract Feb. 4-7, 2009.

Reifenberger, J. et al., Biophys Soc 53rd Ann Meeting (2009) Abstract, Feb. 28, 2009.

Smith, M. et al., "Genomic sequence sampling: a strategy for high resolution sequence-based physical mapping of complex genomes" Nature Genetics (1994) 7:40-47.

Spinella et al., "Tandem arrayed ligation of expressed sequence tags (TALEST): a new method for generating global gene expression profiles" Nucl Acids Res (1999) 27(18):e22-e22.

Velculescu et al. "Serial analysis of gene expression" Science (1995) 270(5235): 484-487.

Volik, S, et al., "End-sequence profiling: sequence-based analysis of aberrant genomes" PNAS (2003) 100(13):7696-7701.

Wiley, G. et al., "Methods for generating shotgun and mixed shotgun/paired-end libraries for the 454 DNA sequencer" Current Protocols in Human Genomics (2009) Chapter 18; Unit 18.1, pp. 1-21.

Technology Spotlight: Illumina Sequencing Technology, current of Oct. 8, 2008, pp. 1-4.

Hormozdiari, et al. "Combinatorial algorithms for structural variation detection in high-throughput sequenced genomes," Genome Research (2009) 19:1270-1278.

Lee, et al. "A robust framework for detecting structural variations in a genome," Bioinformatics (2008) 24:i59-i67.

Margulies, et al., "Genome sequencing in microfabricated high-density picolitre reactors," Nature (2005), 437:376-382.

Pedler, "Occupation Times for Two State Markov Chains," Journ Appl Probability (1971), 8(2):381-90.

Svoboda, et al., "Fluctuation analysis of motor protein movement and single enzyme kinetics," PNAS (1994), 91:11782-86.

International Search Report and Written Opinion dated Oct. 27, 2009 for related case PCT/US2009/001930.

International Preliminary Report on Patentability dated Oct. 7, 2010 for related case PCT/US2009/001930.

International Search Report and Written Opinion dated Nov. 17, 2009 for related case PCT/US2009/001926.

Padegimas, L.S., "Adaptor Ligation-Based Polymerase Chain Reaction-Mediated Walking," Anal Biochem (1998) 260:149-153.

Metzker, M.I., "Emerging Technologies in DNA Sequencing," Genome Research (2005) 15:1767-1776.

Supplementary European Search Report dated Mar. 20, 2012 for related case EP09724672.2.

Ahn et al., "Inhibitory Effects of Novel AP-1 Decoy Oligodeoxynucleotides on Vascular Smooth Muscle Cell Proliferation In Vitro and Neointimal Formation In Vivo," Circulation Research (2002) 90:1325-1332.

(56) References Cited

OTHER PUBLICATIONS

The definition of "consensus sequence". Printed on Aug. 24, 2011.
First Office Action dated Nov. 20, 2012 for related case CN 200980115750.0.
Figures 1A and 1B of US 2007/0087358A1 with the examiner's handwritings. Printed on Oct. 5, 2012.
First Office Action dated Jun. 5, 2013 for related case EP 09724672.2.
Second Office Action dated Sep. 24, 2013 for related case CN 200980115750.0.
First Exam Report dated Jan. 20, 2014 for related case AU 2009229157.
Third Office Action dated Apr. 11, 2014 for related case CN 200980115750.0.
Second Exam Report dated Aug. 22, 2014 for related case AU 2009229157.
Laird et al., "Hairpin-bisulfite PCR: Assessing epigenetic methylation patterns on complementary strands of individual DNA molecules," PNAS (2004) 101(1): 204-209.
Eddy, S.R., "What is a Hidden Markov Model?" Nature Biotechnology (2004) 22:1315-1316.
Kent, W.J., "BLAT—The Blast-Like Alignment Tool," Genome Research (2002) 12:656-664.
Laird et al., "Hairpin-bisulfite PCR: Assessing epigenetic methylation patterns on complementary strands of individual DNA molecules," PNAS (2004) 101(1): 204-209 and supplementary figures 4-7.
Second Exam Report datedMay 27, 2016 for related case CA 2719747.
Verified Complaint of Pacific Biosciences of California, Inc. Under Section 337 of the Tariff Act of 1930 filed with the United States International Trade Commission on Nov. 2, 2016.

\* cited by examiner

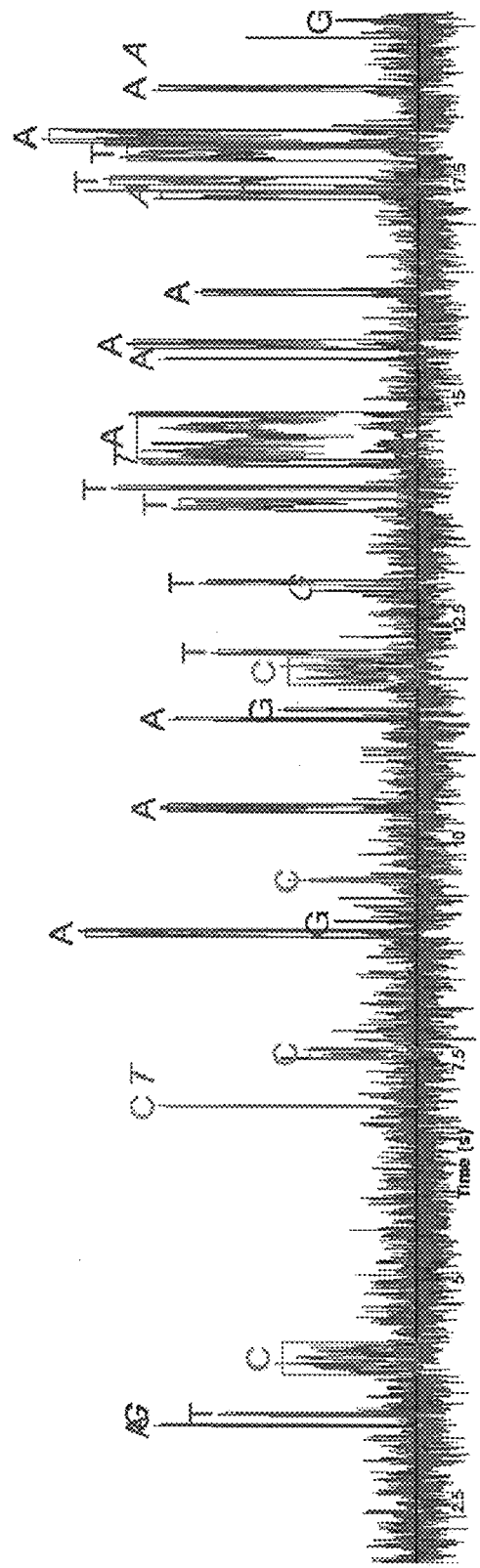
Figure 1, continued

COMPOSITIONS AND METHODS FOR NUCLEIC ACID SEQUENCING

CROSS-REFERENCE TO RELATED APPLICATIONS

This application is a continuation of U.S. patent application Ser. No. 13/866,603, filed Apr. 19, 2013, now U.S. Pat. No. 9,404,146, which is a continuation of U.S. patent application Ser. No. 13/403,789, filed Feb. 23, 2012, now U.S. Pat. No. 8,455,193, which is a continuation of U.S. patent application Ser. No. 12/413,258, filed Mar. 27, 2009, now U.S. Pat. No. 8,153,375, which claims the benefit of Provisional U.S. Patent Application No. 61/072,160, filed Mar. 28, 2008, and Provisional U.S. Patent Application No. 61/099,696, filed Sep. 24, 2008, the full disclosures of which are incorporated herein by reference in their entirety for all purposes.

This application is also related to Provisional U.S. Patent Application No. 61/139,402, filed Dec. 19, 2008, U.S. patent application Ser. No. 12/413,226, filed Mar. 27, 2009, now U.S. Pat. No. 8,143,030, and U.S. patent application Ser. No. 12/383,855, filed Mar. 27, 2009, now U.S. Pat. No. 8,236,499, the full disclosures of which are hereby incorporated herein by reference in their entirety for all purposes.

STATEMENT REGARDING FEDERALLY SPONSORED RESEARCH

Not Applicable.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only 3 KB file (01005908_2014-11-06_SequenceListing.txt).

BACKGROUND OF THE INVENTION

The ability to understand the genetic code that serves as the blueprint for the framework of all life has yielded countless advances in countless areas. From the ability to diagnose disease to the ability to identify evolutionary connections and/or diversity, to the ability to manipulate the genetic framework in the development of new materials and compositions, this understanding has opened doors to innumerable advances that have benefited and will continue to benefit the human race.

Integral to these advances have been the advances in technology directed to the reading and/or characterization of the genetic code. For example, development of nucleic acid sequencing technologies has allowed for the base by base identification of the nucleic acid sequences that make up the genetic code to the point that entire human genomes have been elucidated. Other advances include rapid array based technologies that allow reasonably facile identification of genetic patterns from patients or other biological samples.

With each technological advance, there exist opportunities to further improve the state of the art through advances in related or ancillary technologies associated with those advanced areas. For example, advances in fluorescent dye chemistries have fueled many advances in genetic technologies by permitting simple optical analyses of biological reactions and their products. Likewise, development of microfluidic technologies have provided for advances in fluid and reagent handling to yield a reproducibility that had not been previously achievable through more conventional means.

The present invention is directed to improved processes, systems and compositions used in genetic analysis that can yield enhanced accuracy and ease of use in such analyses.

BRIEF SUMMARY OF THE INVENTION

The present invention provides improved nucleic acid template constructs, compositions, kits and systems incorporating such constructs, and methods for preparing and using such constructs.

In a first aspect, the invention provides a method of determining a consensus sequence of nucleotides in a template nucleic acid segment. The method comprises providing a sense and an antisense strand of the template nucleic acid segment in a contiguous nucleic acid molecule. Both the sense and antisense strands are then sequenced in a polymerase mediated, template dependent sequencing process. The consensus sequence of the target nucleic acid segment is then determined from a sequence of the sense and antisense strands.

In a related aspect, the invention provides methods of sequencing a nucleic acid sequence, that comprise providing a template nucleic acid that comprises a double stranded nucleic acid segment having a first and second end. A first hairpin oligonucleotide connects each strand of the template nucleic acid at the first end, and a second hairpin oligonucleotide connects each strand of the template nucleic acid at the second end. The nucleotide sequence of at least one strand of the template nucleic acid is then determined using a template directed, polymerase mediated nucleic acid sequencing process.

In still another aspect, the invention provides methods of sequencing a nucleic acid sequence, that comprise providing a template nucleic acid that comprises a double stranded segment having a first and second end, where a first hairpin oligonucleotide connects each strand of the template nucleic acid at the first end. The nucleotide sequence of the template nucleic acid is then determined using a template directed, polymerase mediated nucleic acid sequencing process.

In further aspects are provided methods of sequencing a nucleic acid segment, that comprise providing a template nucleic acid segment. The segment comprises first and second complementary nucleic acid strands, a first connecting nucleic acid linking a 3' end of the first nucleic acid segment with a 5' end of the second nucleic acid segment, and a second connecting nucleic acid linking the 5' end of the first nucleic acid strand to the 3' end of the second nucleic acid strand. The template nucleic acid sequence is then contacted with a primer sequence complementary to at least a portion of the template nucleic acid. A template dependent primer extension reaction is then monitored to determine a sequence of nucleotides in the template nucleic acid.

In still a further aspect, the invention provides a method of sequencing a nucleic acid, comprising providing a template nucleic acid comprising a double stranded segment comprising first and second complementary strands and at least a first single stranded oligonucleotide segment linking a 3' end of the first strand to the 5' end of the second strand; and monitoring nucleotides incorporated in a template dependent synthesis reaction to identify a sequence of nucleotides in the first strand, the linking oligonucleotide segment and the second strand.

In other preferred aspects, control sequences are provided within one or more of the liking oligonucleotides or hairpin oligonucleotides described above, such as primer recognition sequences and the like.

In related aspects, the invention provides methods of determining a consensus nucleic acid sequence for a template nucleic acid segment where the sense and an antisense strand of the template nucleic acid segment are provided within a contiguous nucleic acid molecule. The contiguous nucleic acid molecule is contacted and/or complexed with a primer sequence complementary to at least a portion of the contiguous nucleic acid molecule and a polymerase enzyme to provide a nucleic acid synthesis complex, in the presence of a plurality of types of nucleotides or nucleotide analogs, wherein individual nucleic acid synthesis complexes are disposed upon a substrate such that individual complexes are optically resolvable. The sequence of nucleotides or nucleotide analogs incorporated into a nucleic acid synthesis reaction by the individual complexes in a template dependent manner is then monitored and/or detected to determine a nucleic acid sequence of the sense and antisense strands. The nucleic acid sequence of the sense and antisense strands are then used or compared to determine a consensus nucleic acid sequence of the template nucleic acid.

Pooled sample methods are also envisioned by the present invention. For example, in some aspects, the methods of the invention comprise preparing template nucleic acid segments from each of a plurality of discrete nucleic acid samples, wherein the template nucleic acid segments comprise double stranded segments of the nucleic acid samples, a first strand of the double stranded segment being linked to a second strand of the double stranded segment by a linking oligonucleotide, wherein the linking oligonucleotide in each discrete nucleic acid sample comprises a unique, identifiable sequence characteristic. The template nucleic acid segments from the plurality of discrete nucleic acid samples are then pooled, and the pooled template nucleic acid segments are then sequenced to identify the identifiable sequence characteristic, and the nucleic acid sequences deriving from the discrete nucleic acid samples are identified based at least in part on the unique identifiable sequence characteristic identified in the sequencing step.

The invention is also directed to compositions useful in the foregoing methods. In one aspect, the invention provides compositions that comprise a template nucleic acid having a double stranded nucleic acid segment comprising a first strand segment and a second strand segment substantially complementary to the first strand segment, and at least a first linking oligonucleotide segment joining a 3' end of the first strand segment to the 5' end of the second strand segment. The compositions also typically include one or more of a primer sequence capable of hybridizing to at least a portion of the template nucleic acid and initiating polymerase mediated nucleic acid synthesis, and a polymerase enzyme.

The invention also provides template preparation kits useful in practicing the methods of the invention. Such kits typically comprise a first linking oligonucleotide, a primer sequence complementary to at least a portion of the first linking oligonucleotide, and one or more ligation reagents for coupling the first linking oligonucleotide to a 3' end of a first strand of a double stranded template and a 5' end of a second strand of the double stranded template nucleic acid. In addition, such kits will also typically include instruction protocols, and optionally reagents, for coupling the linking oligonucleotide(s) to double stranded target nucleic acid segments deroved from samples for analysis.

The invention also includes systems for sequencing nucleic acid templates. The systems typically comprise a reaction mixture comprising a complex comprising a template nucleic acid, a polymerase enzyme and a primer sequence complementary to at least a portion of the template sequence, wherein the template sequence comprises a double stranded segment having a sense strand and an antisense strand, and at least a first linking oligonucleotide linking a 5' end of the sense strand to the 3' end of the antisense strand, at least a first nucleotide or nucleotide analog bearing a detectable labeling group, and a detection system configured to detect incorporation of the first nucleotide or nucleotide analog into a primer extension product by the polymerase.

Although described in significant detail for purposes of illustration, it will be appreciated that a variety of variations to the invention may be practiced within the scope of the invention.

DETAILED DESCRIPTION OF THE INVENTION

I. General

Figure 1:
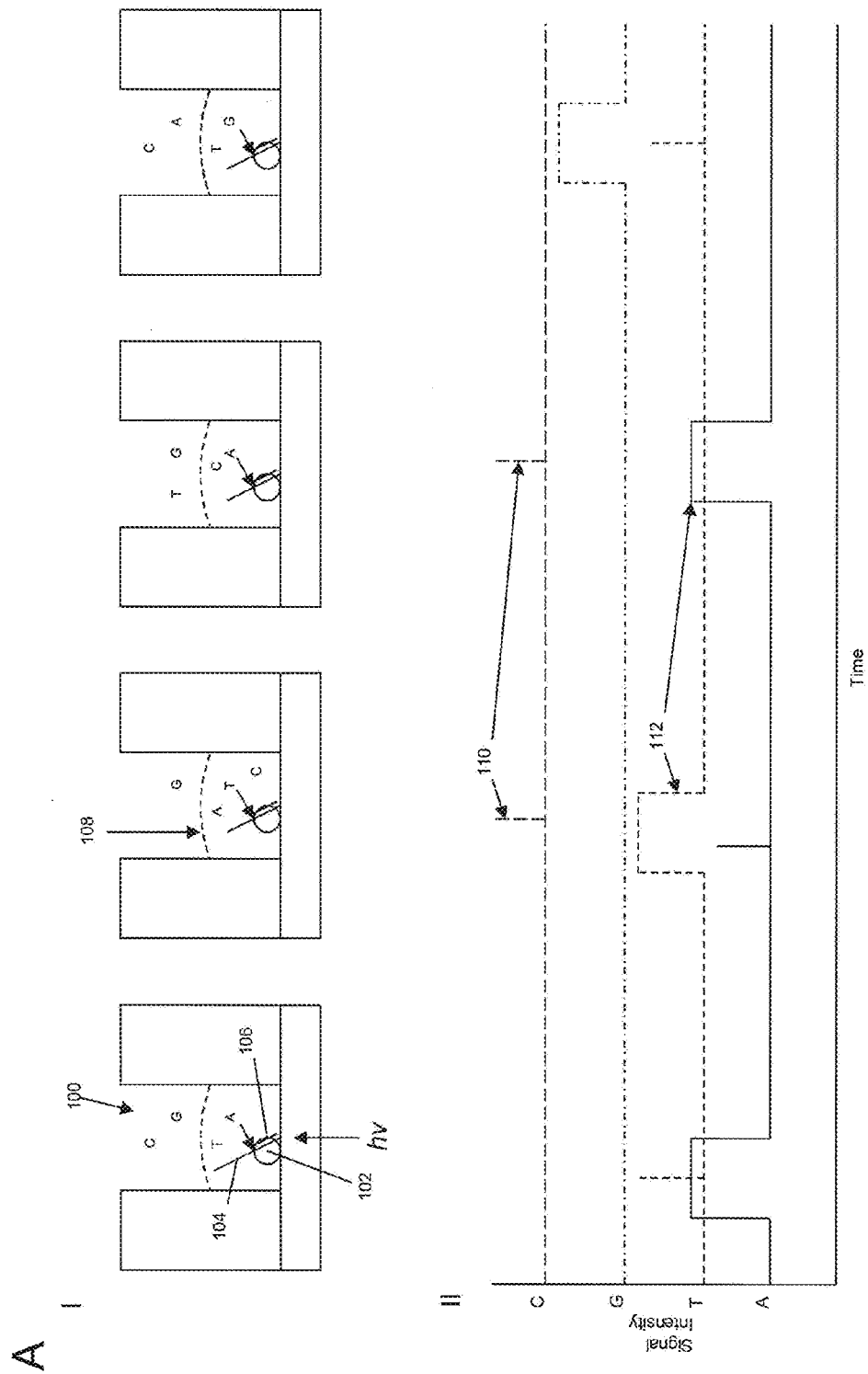
FIG. 1A schematically illustrates a single molecule real time sequencing process.
FIG. 1B illustrates an exemplary short segment of a sequence read using the process schematically illustrated in FIG. 1A.

The present invention is generally directed to improved methods, systems and compositions for carrying out nucleic acid sequence analysis, and particularly sequence analysis that employs template dependent synthesis in identifying the nucleotide sequence of target nucleic acids. Nucleic acid sequence analysis that employs template dependent synthesis identifies individual bases, or groups of bases as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in the ubiquitously practiced four-color Sanger sequencing methods, a population of template molecules is used to create a population of complementary fragment sequences. Primer extension is carried out in the presence of the four naturally occurring nucleotides, and with a sub-population of dye labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the sequence beyond the primer, and are labeled in a manner that permits identification of the terminating nucleotide. The nested fragment population is then subjected to size based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534, incorporated herein by reference in its entirety for all purposes).

Other examples of template dependent sequencing methods include sequence by synthesis processes, where individual nucleotides are identified iteratively, as they are added to the growing primer extension product.

Pyrosequencing is a sequence by synthesis process that identifies the incorporation of a nucleotide by assaying the resulting synthesis mixture for the presence of by-products of the sequencing reaction, namely pyrophosphate. In particular, a primer//template/polymerase complex is contacted with a single type of nucleotide. If that nucleotide is incorporated, the polymerization reaction cleaves the nucleoside triphosphate between the α and β phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891, incorporated herein by reference in its entirety for all purposes).

In related processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. In general, preferred aspects, particularly in accordance with the invention provide for immobilization of the complex via a linkage between the polymerase or the primer and the substrate surface. A variety of types of linkages are useful for this attachment, including, e.g., provision of biotinylated surface components, using e.g., biotin-PEG-silane linkage chemistries, followed by biotinylation of the molecule to be immobilized, and subsequent linkage through, e.g., a streptavidin bridge. Other synthetic coupling chemistries, as well as non-specific protein adsorption can also be employed for immobilization. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes).

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a β, γ, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,056,661, 6,917,726, 7,033,764, 7,052,847, 7,056,676, 7,170,050, 7,361,466, 7,416,844 and Published U.S. Patent Application No. 2007-0134128, the full disclosures of which are hereby incorporated herein by reference in their entirety for all purposes).

One exemplary sequencing process based upon such Single Molecule Real Time (SMRT™) processes is schematically illustrated in FIG. 1. As shown in Panel T of FIG. 1A, a nucleic acid synthesis complex comprising a polymerase enzyme 102, a template sequence 104 and a primer sequence 106 complementary to a portion of the template sequence 104, is provided immobilized within a confined illumination volume (indicated by the dashed line 108), e.g., resulting from the evanescent optical field resulting from illumination of a zero mode waveguide 100, or in a total internal reflectance fluorescence microscope system or other optical confinement system, as described above.

The reaction mixture surrounding the complex contains the four different nucleotides (A, G, T and C) each labeled with a spectrally distinguishable fluorescent label attached through its terminal phosphate group. Because the illumination volume is so small, nucleotides and their associated fluorescent labels diffuse in and out of the illumination volume very quickly, and thus provide only very short fluorescent signals (shown as short pulses 110, in the underlying schematic data plot). When a particular nucleotide is incorporated by the polymerase in a primer extension reaction, the fluorescent label associated with the nucleotide is retained within the illumination volume for a longer time (shown as longer pulses 112). Once incorporated, the fluorescent label is cleaved from the base through the action of the polymerase, and the label diffuses away.

By identifying longer pulses of different spectral characteristics, one can detect, in real time, the identity of each incorporated base as it is being incorporated. An example plot of a short segment of a sequence read from such process is provided in FIG. 1B, with the incorporated nucleotides identified based upon their spectral characteristics, and listed above their respective pulses. Shorter pulses not associated with incorporation tend to be so short that they are not detected by the camera, while pulses from incorporation provide more pronounced and detectable pulses, e.g., as shown in FIG. 1B.

Although described in terms of the specific SMRT™ sequencing process, it will be appreciated that in accordance with the sequencing compositions of the invention, the nucleotides or nucleotide analogs may be detectable by any of a variety of different mechanisms including the presence of fluorescent dye labels coupled to the nucleotide through a β, γ or other more distal phosphate group. For example, as alluded to previously, the nucleotides may bear interacting components, such as one or both members of FRET pairs (dyes, semiconductor nanocrystals, or the like) that interact with their complements elsewhere in the system e.g., on the polymerase, primer, the nucleotide itself, or the substrate. Similarly, these nucleotide analogs may bear other interactive components, such as energy donors or quenchers that alter signal capability of other proximal components. Likewise, non-optical labels may be employed, such as highly charged moieties, magnetic particles or the like, that may be detected by electrochemical systems, e.g., ChemFET sensors, nanopore sensors (see, e.g., Clarke et al., Nature Nanotechnology, Published online: 22 Feb. 2009|doi: 10.1038/nnano.2009.12), and the like. In addition, the nucleoside polyphosphates described herein may generally include tri, tetra, penta, hexa or other phosphate chain lengths incorporatable by the polymerases used. Such compounds, including those bearing detectable labeling groups are described in, e.g., U.S. Pat. No. 7,041,812, the full disclosure of which is incorporated herein by reference in its entirety for all purposes.

For a number of approaches, e.g., single molecule methods as described above, it may be desirable to provide the nucleic acid synthesis complexes in individually optically resolvable configurations, such that the synthesis reactions of a single complex can be monitored. Providing such complexes in individually resolvable configuration can be accomplished through a number of mechanisms. For example, by providing a dilute solution of complexes on a substrate surface suited for immobilization, one will be able to provide individually optically resolvable complexes (See, e.g., European Patent No. 1105529 to Balasubramanian, et al., which is incorporated herein by reference in its entirety for all purposes. Alternatively, one may provide a low density activated surface to which complexes are coupled (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation.

II. Contiguous Double Stranded Templates

The present invention provides novel template configurations and methods for exploiting these compositions in template directed sequencing processes. While these compositions and methods have utility across all of the various template directed processes described herein, for ease of discussion, they are being primarily discussed in terms of preferred single molecule, real-time sequencing processes, in which they provide myriad benefits. In particular, the present invention is generally directed to nucleic acid sequences that employ improved template sequences to improve the accuracy of sequencing processes. For example, in at least one aspect, the template compositions of the invention are generally characterized by the presence of a double stranded segment or a pair of sub-segments that are internally complementary, i.e., complementary to each other. In particular contexts, the target nucleic acid segment that is included within a template construct will typically be substantially comprised of a double stranded segment, e.g., greater than 75%, or even greater than 90% of the target segment will be double stranded or otherwise internally complementary. For ease of discussion, these double stranded target segments, whether entirely complementary or predominantly complementary, e.g., having overhang regions, or other non-complementary portions such as secondary loop structures or the like, are referred to herein as complementary or substantially complementary. Where complete complementarity between two strands is intended and required from the context or explicitly, the phrase 'completely complementary' or 'entirely complementary' will be used.

The strands that make up the double stranded segment, and/or the internally complementary strands are, in the context of the invention, at least partially contiguous, and in preferred aspects are completely contiguous. As used herein, two strands are partially contiguous if they are joined at at least one end of each strand, and are completely contiguous if they are joined at both ends, resulting in an overall circular strand configuration, where such joining may be direct coupling of the ends of the sense and antisense strands, or through a linking oligonucleotide. As will be appreciated, the term circular, when referring to the strand configuration merely denotes a strand of a nucleic acid that includes no terminal nucleotides, and does not necessarily denote any geometric configuration.

Examples of template configurations of the invention that are partially and completely contiguous are schematically illustrated in FIGS. 2A and 2B, respectively. In particular, as shown in FIG. 2A, a partially contiguous template sequence 200 is shown which includes a double stranded portion, comprised of two complementary segments 202 and 204, which, for example, represent a target sequence or portion thereof. As shown, the 3' end of segment 202 is linked to the 5' end of segment 204 by linking oligonucleotide 206, providing a single stranded portion of the template, and yielding a partially contiguous sequence. By comparison, as shown in FIG. 2B, a completely contiguous template sequence 210 is shown. Sequence 210 includes a double stranded portion again comprised of two complementary segments 212 and 214. As with the partially contiguous sequence of FIG. 2A, the 3' end of segment 212 is joined to the 5' end of segment 214 via oligonucleotide 216 in a first single stranded portion. In addition, the 5' end of segment 212 is joined to the 3' end of segment 214 via linking oligonucleotide 218, providing a second single stranded portion, and yielding a completely contiguous or circular template sequence.

In a typical sequencing process, a double stranded target nucleic acid, e.g., a nucleic acid for which sequence information is desired, is converted to a template configuration of the invention. Typically, this involves fragmentation of a population of a larger double stranded nucleic acid, e.g., a genome, plasmid, or portion thereof, or the like, into pools of smaller, overlapping double stranded target nucleic acids or nucleic acid fragments. The double stranded fragments are then processed to provide the linking oligonucleotides described above and in greater detail, below. A number of methods, as set forth herein, may be employed to provide the linking oligonucleotides connecting the sense and antisense strand. In one simple example, exogenous hairpin adapter sequences are used and simply ligated to the end(s) of the double stranded fragments to form such linking oligonucleotides. Such exogenous hairpin adapters will typically include two complementary nuclei acid sequence segments at opposing ends of a longer sequence, where they are separated by another stretch of non-complementary nucleotides. The result is a structure that includes a double stranded stem structure coupled to the single stranded loop. Examples of such hairpin structures have been described previously (See, e.g., U.S. Pat. Nos. 6,498,023, 6,451,563, and 7,368,265, the full disclosures of which are incorporated herein by reference in their entirety for all purposes). Generally, such structures are readily synthesized using conventional nucleic acid synthesis techniques. A number of other methods employ alternate approaches to generating the linking oligonucleotide structures, and are described below.

Following sequence determination of the various target nucleic acid fragments, the sequence of the starting target nucleic acid is then determined by identifying and aligning overlap between sequence data from the various different overlapping fragments.

The templates of the invention provide numerous advantages over simple linear template sequences, and even other circular template sequences (See, e.g., U.S. Pat. No. 7,302,146 for a discussion of circular templates for sequencing applications, the full disclosure of which is incorporated herein by reference in its entirety for all purposes). In particular, as with circular templates, the template configurations of the invention allow for single molecular consensus sequence determination, where sequencing a given template provides duplicative or replicate data of the sequence information obtained, and thereby improves accuracy over linear templates by providing multiple reads for a given template sequence or sequence portion, that can be used to derive consensus sequence data from a given template sequence and/or for specific base locations within such sequence. In these templates, the potential for consensus sequence determination is provided, in one respect, by virtue of the circular nature of the overall template structure, for a completely contiguous template, allowing repeated processing of the same molecule to obtain consensus base calls and/or a consensus sequence. In addition or alternatively, the templates of the invention, by virtue of their inclusion of double stranded segments, provide consensus sequence determination through the sequencing of both the sense and antisense strand of such sequences (in both the partially and completely contiguous configurations). Although described herein primarily as consensus sequence determination, it will be appreciated that the level of consensus determination extends to the individual base level for a given base position within a sequence, which, when placed in sequence context yields consensus sequence data for a particular sequence. Thus, the invention also encompasses consensus base calling (nucleotide identification) for individual positions within a template sequence.

Figure 2:
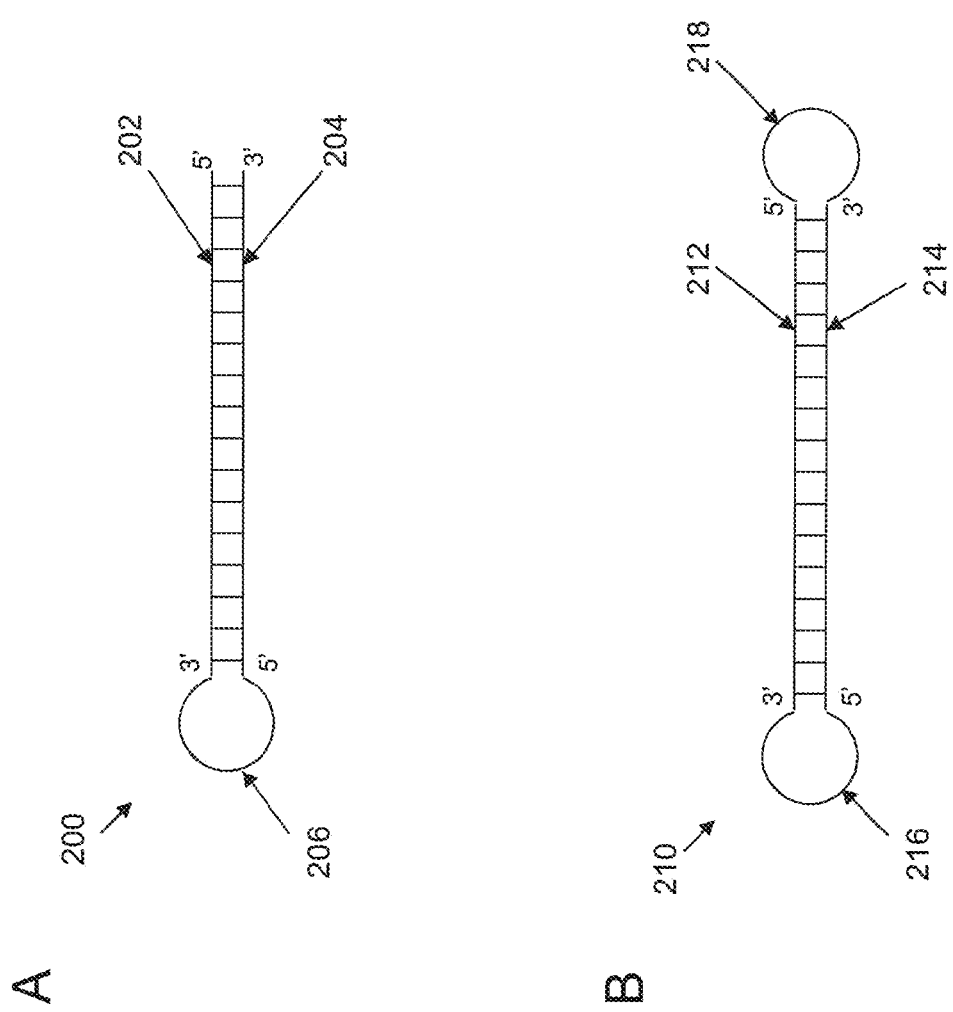
FIGS. 2A and 2B illustrate two exemplary embodiments of template constructs used in the present invention.
Figure 3:
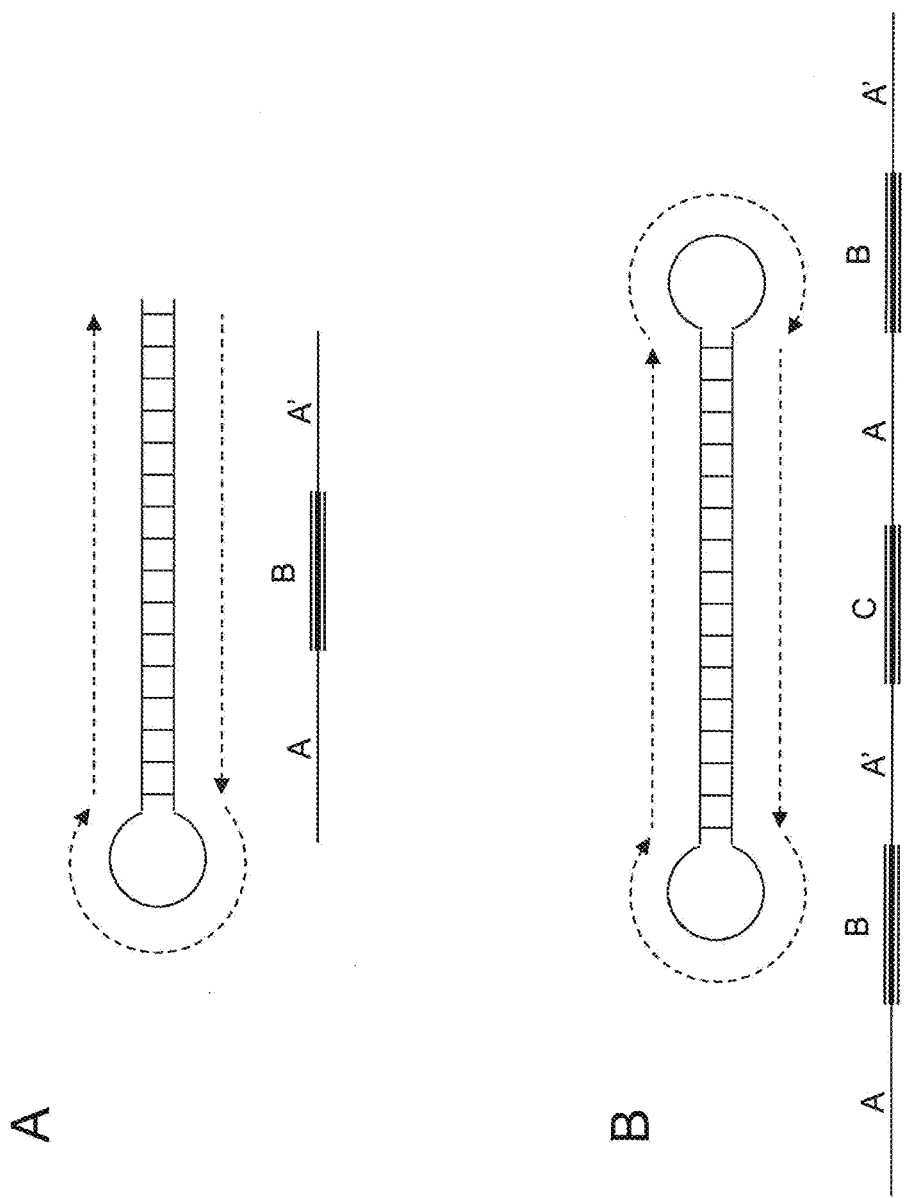
FIGS. 3A and 3B schematically illustrate redundant or consensus sequencing using the constructs shown in FIGS. 2A and 2B, respectively.

By way of example, with respect to a partially contiguous template shown in FIG. 2A, obtaining the entire sequence, e.g., that of segments 202, 204 and 206 provides a measure of consensus sequence determination by virtue of having sequenced both the sense strand, e.g., segment 202, and the antisense strand, e.g., segment 204. In addition to providing sense and antisense sequence reads from a single template molecule that can be sequenced in one integrated process, the presence of linking segment 206 also provides an opportunity to provide a registration sequence that permits the identification of when one segment, e.g., 202, is completed and the other begins, e.g., 204. Such registration sequences provide a basis for alignment sequence data from multiple sequence reads from the same template sequences, e.g., the same molecule, or identical molecules in a template population. The progress of sequencing processes is schematically illustrated in FIG. 3A. In particular, as shown, a sequencing process that begins, e.g., is primed, at the open end of the partially contiguous template, proceeds along the first or sense strand, providing the nucleotide sequence (A) of that strand, as represented in the schematic sequence readout provided. The process then proceeds around the linking oligonucleotide of the template, providing the nucleotide sequence (B) of that segment. The process then continues along the antisense strand to the A sequence, and provides the nucleotide sequence (A'), which sequence can be used to derive or determine a consensus sequence for the sense strand, as its antisense counterpart. As noted, because the B sequence may be exogenously provided, and thus known, it may also provide a registration sequence indicating a point in the sequence determination at which the sequencing reaction, and thus, the sequence data being obtained from the overall template construct, transitions from the sense to the antisense strands.

With respect to completely contiguous or circular template sequences configured in accordance with the invention, the potential for obtaining replicate sequence read data from which one may assemble consensus sequence information, is further increased. In particular, as with the partially contiguous sequences shown in FIG. 2A, the completely contiguous sequences also provide sense and antisense sequence data. In addition, such templates provide for the potential for iterative sequencing of the same molecule multiple times, by virtue of the circular configuration of the template. Restated, a sequence process may progress around the completely contiguous sequence repeatedly obtaining sequence data for each segment from the complementary sequences, as well as sequence data within each segment, by repeatedly sequencing that segment. All or portions of such sequence data is then useful in deriving a consensus sequence for the template and its various segments. This is schematically illustrated in FIG. 3B, again with a representative illustration of a sequence readout provided. As shown, a sequencing process that is primed at one end, e.g., primed within one linking oligonucleotide sequence, e.g., linking oligonucleotide 218 of FIG. 2, proceeds along the first or sense strand 214, again providing the nucleotide sequence A of that strand. The sequence process then proceeds around the first linking oligonucleotide, e.g., linking oligonucleotide 216 from FIG. 2, to provide the nucleotide sequence B of that segment of the template. Proceeding along the antisense strand, e.g., segment 212 of FIG. 2B, provides the nucleotide sequence A', which is again, complementary to sequence A. The sequencing process then continues around the template providing the nucleotide sequence for the other linking oligonucleotide, e.g., linking oligonucleotide 218 of FIG. 2B, where the illustrated sequencing process began, providing nucleotide sequence C. Because the template is circular, this process can continue to provided multiple repeated sequence reads from the one template, e.g., shown as providing a second round of the sequence data (A-B-A'-C-A-B-A'). Thus, sequence redundancy comes from both the determination of complementary sequences A and A', and the repeated sequencing of each segment.

As will be appreciated, in iteratively sequencing circular templates, strand displacing polymerases, as discussed elsewhere herein, are particularly preferred, as they will displace the nascent strand with each cycle around the template, allowing continuous sequencing. Other approaches will similarly allow such iterative sequencing including, e.g., use of an enzyme having 5'-3' exonuclease activity in the reaction mixture to digest the nascent strand post synthesis.

As will be appreciated, and as noted elsewhere herein, the repeated sequencing of a given sequence of nucleotides, whether as the identical sequence or as a complement to that sequence, and whether as an individual sequence or as a repeating copy of that sequence, e.g., in a concatameric orientation, provides the ability to assemble a consensus sequence for that sequence segment. In particular, one can employ iterative sequence reads of a given sequence, and/or reads of a sequence and its complement, to establish a consensus sequence of nucleotides for that sequence segment. Rephrased, each base called in a sequence can be based upon a consensus base call for that particular position based upon multiple reads at that position and/or reads at that position and it's complement in an antisense strand. These multiple reads are then assembled or compared to provide a consensus determination of a given base at a given position, and as a result, a consensus sequence for the particular sequence segment.

Although referred to herein as comparing or assembling the sequence data from multiple reads of a given sequence, and/or from the sense and antisense strands of the sequence, it will be appreciated that any method of assigning a consensus determination to a particular base call from multiple reads of that position of sequence, and/or to a provide an overall consensus sequence for that segment, will be envisioned and encompassed by the term "compare". Such methods include actual side-by-side comparisons, scoring methods whereby calls of iterative reads or from complementary sequences are scored by the number of occurrences, and optionally or alternatively additional signal/base calling metrics, to complex algorithms for assigning a base call from multiple indications of the base at a given position.

By way of example, some such methods generally encompass algorithms that combine data derived from a base with data derived from other determinations of that sequence position, whether in a duplicate sequence read (from the same or a duplicate sequence segment), or from its complement in the opposite strand.

One category for combination of such data includes a first step of determining the association between signals originating from a base and signals originating from other reads at that position or from its complement, followed by a second step of combining those data. Methods for determining such association are known in the art and include heuristic methods for multiple-sequence alignment, optimal methods for multiple sequence alignment, and hidden Markov models, and in the broadest sense all of these algorithms have in common that they seek to align corresponding bases in the input reads. Such associations are not limited to basecalls alone and can be derived from inherent features of the signal such as channel, amplitude, width, or other time-dependent patterns associated with the signals. Algorithms known in the art for the combination of data from pre-associated bases include Plurality, Quality-weighted Plurality, Bayesian methods, and machine learning approaches (neural networks, self-organizing maps), and generally these algorithms have in common that they classify the presented evidence into a consensus basecall, often with an associated probability of error. In this category of algorithm, there are numerous variations that include additional steps before, after and between these steps that have beneficial impacts such as improvement the quality of results reduction in computation time. For example, in one such method data associated with other bases in said first step are referenced during or after said second step in order to evaluate the possibility that errors were made in said association. The association step can be made between reads from a single molecule, or between reads from different molecules.

In another method for combination of data, a consensus is first established for one sequence read, e.g., a sense strand, and another consensus sequence is established for another read, e.g., the antisense strand. These sequences can be established by methods known in the art including heuristic methods for multiple-sequence alignment, optimal methods for multiple sequence alignment, or hidden Markov models in combination with a consensus determination algorithm such as Plurality, Quality-weighted Plurality, Bayesian methods, or machine learning approaches (neural networks, self-organizing maps). These consensus sequences can then be associated and combined via algorithms such as heuristic methods for multiple-sequence alignment, optimal methods for multiple sequence alignment, or hidden Markov models in combination with a consensus determination algorithm such as Plurality, Quality-weighted Plurality, Bayesian methods, or machine learning approaches (neural networks, self-organizing maps).

Another class of algorithms performs the association and combination in a single step. These methods proceed from a probabilistic model which seeks to find the most likely template given the observed reads. Such models belong in the category of probabilistic graphical models and include Bayesian networks, hidden Markov models, neural networks, and conditional random fields. The input to such a model is not limited to basecalls alone, but can include local or global measures of the individual sequence qualities, sequence context, and characteristic features of the raw signals. Consensus determination by these models proceeds by finding the template which maximizes the likelihood of the observed reads under the constraints of the probabilistic model. It is usual that such methods can produce one or more likely consensus sequences and provide scoring information for ranking the likelihood of each sequence. For purposes of discussion herein, the methods by which a consensus sequence is called from repeated sequence reads of a given segment (including reads of the sense and antisense strands), are referred to generally herein as "comparing."

In addition to the aspects related to consensus sequence determination, set forth above, there are a number of other significant advantages of the template structures of the invention. For example, with respect to completely contiguous constructs, a number of advantages of these templates derive from their basic circular structure. For example, because the completely contiguous templates of the invention are circular in structure, one can initiate a polymerase mediated synthesis process and sequencing at any point in the template, with the expectation that the entire template will be sequenced or at least sequenceable. In contrast, with linear template sequences, one faces the risk of missing upstream portions of the template for sequencing. As a result, sequence initiation processes, also referred to as "hot start" processes, are typically used when employing linear templates, e.g., withholding a key reagent until one is ready to initiate synthesis and sequence data collection.

In addition to obviating the need for sequencing initiation processes, the use of such circular templates also provides the ability to obtain sequence data from disparate portions of the same template molecule without necessarily requiring that one obtain the entire sequence of the template. For example, in single molecule sequencing processes, or in sequencing processes that employ populations of identical template molecules, one can obtain multiple subsets of sequence information on the template molecule with the understanding that each subset is contextually related to each other subset, e.g., contained within the same template sequence. This aspect of the invention is discussed in greater detail below with reference to paired end sequencing processes.

For example, because of the structure of these templates, one can effectively make a circular template out of any length of target nucleic acid. In particular, because one can use exogenous linking sequences, which may include their own self complementary segments, one can effectively circularize very short double stranded oligonucleotide fragments. In particular, circularization of a single stranded nucleic acid segment typically requires a sequence that is at least 30 nucleotides in length, with probable additions of adapter sequences and the like, in order to circularize the segment. The templates of the invention, on the other hand, can be used to convert a target nucleic acid of much shorter length, into a circular template. In particular, target sequences equal to or shorter than 50 bases, 20 bases, or even 10 bases, can readily be converted to a circular template. In addition, the converse is also true in exploiting the template constructs of the invention. In particular, using these configurations, one can effectively provide completely contiguous or "circular" templates from very large double stranded target sequences, without many of the difficulties attendant to the production of larger circular nucleic acids. In particular, one can effectively employ very large double stranded inserts, e.g., greater than 100 base duplexes (total nucleotides), greater than 500 base duplexes, greater than 1000 base duplexes, greater than 5000 base duplexes, and even greater than 10,000 base duplexes in producing a template construct.

The template configurations of the invention are also advantageous in that they do not require working with single stranded nucleic acid sample segments. For example, in cases where one is presented with target nucleic acids that are double stranded, e.g., PCR products, genomic fragments, or the like, one can readily convert these to template molecules of the invention, by providing linking segments that couple the 3' end of one strand to the 5' end of the other strand, and vice versa. As noted above, relatively small double stranded segments, e.g., having 50 or fewer base pairs, 20 or fewer base pairs, or even 10 or fewer base pairs, may be readily incorporated into circular templates in accordance with the invention. Typically, circularization of double stranded segments, because of their structural rigidity, requires segments on the order of several hundred base pairs in length. Conversely, circularization of large single stranded nucleic acids.

The template configurations of the invention, also provide advantages by virtue of the presence of both single stranded and double stranded portions within the same template. By way of example, the single stranded linking oligonucleotides, not only can be selected to present a specific primer recognition sequence, they also provide the primer and polymerase binding site in a required single stranded conformation, thus allowing primer annealing and polymerase complexing, without the need for any denaturing steps. While advantages over other double stranded templates are readily apparent, priming advantages also exist with respect to other single stranded templates. In particular, in cases where one is employing a polymerase that binds single stranded segments with high affinity, one can better control polymerase binding when only a relatively small portion of the template is single stranded, e.g., directing binding to the desired priming sites. A variety of examples of such polymerases are available, including, e.g., phi29 type polymerases (See, e.g., U.S. Pat. Nos. 5,001,050, 5,576,204, the full disclosures of which are incorporated herein by reference in their entirety for all purposes) and derivatives thereof, as well as other strand displacing polymerases (See, e.g., International Patent Application Nos. WO 2007/075987, WO 2007/075873, WO 2007/076057, incorporated herein by reference in their entirety for all purposes).

Notwithstanding the foregoing, however, while the single stranded portion of the template is often and advantageously employed as the priming site, in some cases, priming can also be carried out within the double stranded portions of the template, e.g., allowing the use of primers specific for the target sequence.

In addition, they provide an element of controllability in presenting primer binding sites that other single stranded templates may lack. In particular, selection of primer sequences for large target nucleic acids can be difficult, as one typically wants to avoid random and multiple priming of the template material. Accordingly, primer sequences typically must be carefully selected to be highly specific, requiring relatively long sequences. However, by providing only a minimal amount of single stranded material within a template population, e.g., those portions within the linking oligonucleotides, and further enhanced by the knowledge of those sequences, one can utilize substantially shorter primers while retaining specificity to the desired priming location, as the larger target fragments, as double stranded nucleic acids, will be unavailable for primer binding. Further, one can utilize primers that are engineered to provide substantially higher affinity for the template, without the concurrent concern that such higher affinity to the template will yield a higher rate of random or non-specific priming. In particular, one can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template.

In addition to the foregoing advantages, partially contiguous templates of the invention provide a number of specific advantages, as well. By way of example, in some cases, a partially contiguous template may be provided in which, in addition to the linking oligonucleotide segment, a portion of the target segment may exist as a single stranded segment. Depending upon which strand is provided as a single stranded segment, e.g., the 5' or 3' end of the template, different alternatives for sequencing, and particularly, priming, are presented. For example, in the configuration where the single stranded portion is that which includes the 3' terminus, the single stranded portion provides a primer binding location in order to sequence the remainder of the template. In contrast, by providing the 5' end of the template as the single stranded portion, the template itself provides the primer for polymerase mediated synthesis and thus, sequencing. In other configurations, a gap or nick (as described elsewhere herein) may be provided within a double stranded segment of an otherwise completely contiguous template structure, to provide a priming site for polymerase attachment.

Figure 4:
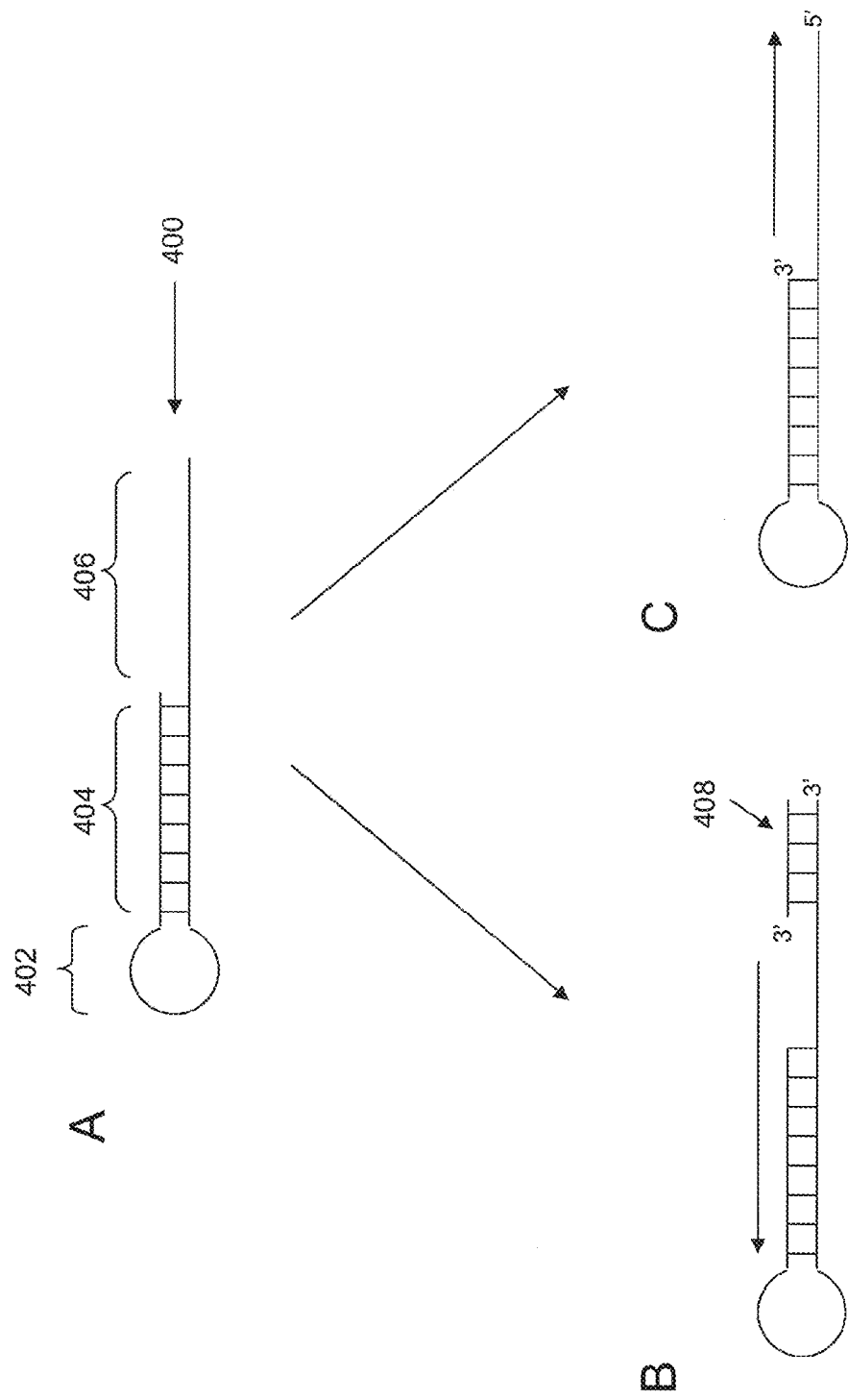
FIGS. 4A, 4B and 4C illustrate alternate template constructs and their application in sequencing processes.

These configurations and the alternative synthesis/sequencing approaches are schematically illustrated in FIGS. 4A, 4B and 4C. As shown in FIG. 4A, a partially contiguous template 400 is provided that includes a double stranded portion 402, a single stranded linking oligonucleotide portion 404. A portion of the target sequence is also provided in single stranded form, e.g., segment 406. FIG. 4B illustrates the configuration where the single stranded portion is the 3' portion of the template. In particular, one can use the single stranded segment 406 as a binding location for a primer for synthesis and sequencing, e.g., primer 408. Sequencing then proceeds along the remainder of the template, as indicated by the arrow.

In contrast, as indicated in FIG. 4C, the 5' portion of the template is provided as the single stranded segment 406. As such, the double stranded portion of the template 402, functions as a self primer to allow synthesis and sequencing of the single stranded portion 406, as indicated by the arrow. Additional components could be added to the template structure, e.g., to protect the 3' end from exonuclease digestion, e.g., a phosphorothioate, etc.

In addition to all of the foregoing advantages, and relative to the sense/antisense consensus sequence determination aspects of the template configurations of the invention, the templates described herein, may be applied in sequencing processes that utilize fewer than four differentially detectable events for incorporation of the four different nucleotides. In particular, many sequencing processes employ the four different nucleotides each labeled with a distinct and separately detectable label group, e.g., a fluorescent label. In the past, there have been proposals for performing sequencing operations using fewer than four distinct labeling groups. By way of example, a proposed process employed nucleotides labeled with only two distinct labels, where one label is associated with a particular nucleotide, while the other is associated with all other nucleotides. The label on three of the nucleotides is merely provided to provide relative context or spacing between each of the specifically labeled nucleotides. Complete sequence information, however, would require passing through the template at least three, and most likely four times, to provide a specific label for each base.

In the context of the templates of the invention, because of the presence of both the sense and antisense sequences within the template construct, a single pass through a given template could provide complete sequence information using fewer than four distinct labeled events. In particular, by providing two, non-complementary nucleotides, e.g., A and G, with the same label, and providing a second and third label on the T and C nucleotides, one could obtain the complete sequence by comparing the sense and antisense strands to identify which of the identically labeled bases would be an A and which would be a G, by virtue of its complementary to a specifically identified T or C from the other strand. Similarly, one could effectively obtain complete target sequence information from sense and antisense strands using only two distinguishable labels. In particular, one could associate a first label with one set of the four nucleotides, e.g., A and G, while providing a second label on the other set, T and C for sequencing the sense strand. The labeling configuration could then be switched for sequencing the antisense strand, e.g., the first label linked to the A and C bases and the second label linked to the G and T bases. Comparison of the sequence data would then yield the precise identity of each base. In operation, sequencing could be carried out in the presence of the first labeling configuration and then new reagents would be introduced bearing the second labeling configuration, e.g., in a wash step. As will be appreciated, repeated sequencing would, again, provide for the ability to obtain consensus sequence data, as described above.

III. Additional Sequences

In addition to advantages of consensus potential within each template molecule, and the other advantages described above, the template configurations have a number of different advantages for many or all of the different template dependent sequencing processes associated with the potential for the addition of other sequences into the template molecule.

For example, in some cases, connecting or linking sequences may be selected and/or observed as registration sequences to provide landmarks within the overall template sequence, e.g., to provide alignment of iterative sequence data, to identify the level of coverage in a consensus sequence read, to identify points in a sequencing process where one is progressing into a consensus sequence, e.g., an antisense strand or repeated sequence of the entire template, and the like.

In addition, such sequences may provide control opportunities for the sequencing process using such templates. For example, and preferably in the case of completely contiguous sequences, as discussed previously, one may incorporate primer recognition sequences within the connecting oligonucleotides to initiate polymerization. As noted previously, the flexibility as to the types and configuration of the primer sequences is increased by virtue of immunity from binding to the target portion of the sequence, which exists as a double stranded segment.

Additional control sequences may also be provided, e.g., sequences that allow control over the initiation of synthesis, e.g., through a hybridized probe or reversibly modified nucleotide, or the like (See, e.g., U.S. Patent Application No. 2008-0009007, the full disclosure of which is incorporated herein by reference in its entirety for all purposes.). Other control sequences may include binding sites for transcription factors. For example, repressor binding regions may be provided as control sequences within the linking oligonucleotides, such as the lac repressor recognition sequence, which when bound by the lac repressor protein, has been shown to block replication both in vivo and in vitro. Reinitiation of replication is accomplished through the addition of appropriate initiators, such as isophenylthiogalactoside (IPTG) or allolactose. Other DNA binding protein recognition sites may also be included within the linking oligonucleotide to allow control over the progress of synthesis using the templates of the invention. Other controllable elements may include the use of non-natural bases (also termed $5^{th}$ bases) within the linking region which are not paired with any of the four basic nucleoside polyphosphates in the synthesis reaction. Upon encountering such a base, the polymerase would pause until its own particular complement was added to the reaction mixture. Likewise, an engineered pause point within the linking oliogonucleotide region could include a "damaged" base that causes a stop in replication until repair enzymes are added to the mixture. For example within the linking oligonucleotide could be included a base position having a pyrimidine dimer. Such compounds would cause the replication complex to pause. Addition of the photolyase DNA repair enzyme would repair the problem location and allow replication, and sequencing to continue.

Recognition sites for a variety of other oligonucleotide probes are also optionally incorporated into these linking sequences, e.g., hybridization sites for labeled probes, molecular beacons, TaqMan® probes, Invader® probes (Third Wave Technologies, Inc.), or the like, that can be used to provide other indications of the commencement of synthesis. Additionally, non-native bases that interact/complement other non-native bases may be used to provide an initiation point for synthesis and sequencing.

In some cases, it may be desirable to provide endonuclease recognition sites within the linking oligonucleotide, which can allow for a mechanism to release a given template sequence from a synthesis reaction, i.e., by linearizing it, and allowing the polymerase to run off the linear template, and/or to expose the template to exonuclease activity, and thus terminate synthesis through removal of the template. Such sites could additionally be exploited as control sequences by providing specific binding locations for endonucleases engineered to lack cleavage activity, but retain sequence specific binding.

In some cases, nicking sites, e.g., sites recognized by nicking endonucleases, may be included within a portion of the template molecule, and particularly within the double stranded portion of the template, e.g., in the double stranded fragment portion or in the stem portion of an exogenous hairpin structure. Such nicking sites provide a break in one strand of a double stranded sequence, to present a priming location for, e.g., a strand displacing polymerase enzyme. In the context of the templates of the invention, the nicking site may be provided for example, within a hairpin adapter that is annealed and ligated to a double stranded target fragment. Other methods as described below may similarly introduce nicking sites. Alternatively, nicking endonucleases may be applied randomly against the target fragment to initiate priming. A variety of nicking enzymes and their recognition sequences are known in the art, with such enzymes being generally commercially available, e.g., from New England Biolabs. Alternatively, one may employ pre-nicked double stranded segments in the hairpin adapters used in preparing the template construct. Such nicks could include gaps in the double stranded segments of from 0 to 20 nucleotides, depending upon the need of the application.

IV. Template Structures

In addition to the basic configuration of the templates of the invention, as described and illustrated previously, a number of other structural considerations may also be incorporated into the templates of the invention. For example, the relative size or length of the overall template molecule, as well as the sizes of the various segments that make up the template, may be selected for optimal benefit in given applications.

In general, the overall size of the template will be dictated by the application in which the template will be used. By way of example, where a given template is being subjected to a polymerase mediated sequencing process, limitations on the readlength for the particular system may be factored into the selection of the overall template size, e.g., to ensure complete, and preferably redundant sequencing of the entire template. For example, where a given polymerase mediated sequencing process has readlength of 1000 bases, a requirement for at least 2× redundant sequencing would dictate a template of 500 bases, including both the linking oligonucleotides and the target segment. Of course, because the sequence of the start/finish linking oligonucleotide may be known and is not relevant to determination of the target sequence, it may not be necessary to obtain 2× redundancy of that segment, and thus a consequent increase in template size could be tolerated. For purposes of certain redundant sequencing applications, a template that is between about 50 and about 500 bases may be desired. In other applications, where longer readlengths are obtained, or in non-redundant applications, templates that are from about 200 to about 50,000 bases in length may be used. Although described in terms of specific lengths, it will be appreciated that a variety of different template sizes may be employed for a variety of different specific applications.

In addition to readlength considerations, an overall template may be subject to application-specific structural requirements. For example, where a sequencing process employs nanostructured reaction regions, it may be desirable to provide smaller template molecules to ensure rapid diffusion into and out of the reaction region.

The size of the target portion may also be varied depending upon the application in which the template is being used. For example, in genomic sequencing applications, e.g., de novo or resequencing processes, longer target segments will be desired in order to reduce the level of duplicate coverage that is required among different fragments. In particular, the ability to sequence template fragments that are in excess of 100, preferably in excess of 200, still more preferably, in excess of 500, in excess of 1000, and even in excess of 10,000 nucleotides in length, provides substantial benefits in genomic assembly from overlapping fragments. In particular, the level of required duplicate coverage for identical sequence portions is substantially reduced by increases in the size of any individual sequence read.

In addition to advantages for long read length sequencing applications, larger target segments also provide advantages in the ability to provide paired end sequence data using single molecule sequencing processes. Briefly, in many sequencing processes, one can obtain sequence context of relatively short sequence reads, by reading the sequence that is disposed at opposing ends of a large target fragment. Typically, this involves the sequencing of a relatively short stretch of bases at either end of a double stranded target segment. From the knowledge that these two sequences are derived from the same target molecule, and optionally, from a general understanding of the size of the fragment, one obtains contextual data for the short sequences. While paired end sequencing has distinct advantages in short readlength sequence processes in providing two pieces of sequence information from a given target, it also is useful in longer read sequence technologies as it provides the ability to obtain contextual "waypoints" for very large nucleic acid sequences, which can be used in aligning sequence data.

In the context of the template sequences of the invention, one can readily obtain sequence data from opposing ends of a single template by first obtaining sequence data from a first end of the target portion. One may then wait an appropriate amount of time for a given sequencing system, for the process to reach the opposing end of the target, and begin obtaining sequence data again. As a result, one has obtained sequence data from paired ends of the same target. As will be appreciated, the foregoing process has particular use where an overall readlength of a sequencing system is impacted by the data collection process, e.g., through the continuous illumination of the complex (See, e.g., U.S. Patent Application No. 2007-0161017, the full disclosure of which is incorporated herein by reference in its entirety for all purposes). Alternatively, one may employ a reaction stop point within the template sequence, such as a reversibly bound blocking group at one location on the template, e.g., on the single stranded portion that was not used in priming. By way of example, and with reference to FIG. 2B, following initial sequencing from the original priming location, e.g., at single stranded linking oligonucleotide portion 216, through one end of the sense strand 214, the data acquisition may be switched off, allowing the polymerase to proceed around the template, e.g., through sense strand 214, to the other previously single stranded portion, e.g., linking oligonucleotide portion 218. The incorporation of a synthesis blocking group coupled to the linking oligonucleotide will allow control of initiation of the sequencing of the opposing end of the antisense strand, e.g., strand 212. One would thereby obtain paired end sequence data for the overall double stranded segment. A variety of synthesis controlling groups may be employed, including, e.g., large photolabile groups coupled to the nucleobase portion of one or more bases in the single stranded portion, which inhibit polymerase mediated replication, strand binding moieties that prevent processive synthesis, non-native nucleotides included within the primer (as described in greater detail elsewhere herein), and the like.

Alternatively, one may employ primer recognition sites on each of the two linking oligonucleotide sequences employed in a population of like template molecules, e.g., PCR products. By then separately sequencing from each end, one can obtain sequence data from different ends of the same double stranded fragment, and thus obtain the paired end data desired.

In contrast, for diagnostic sequencing applications, it may be necessary only to provide sequence data for a small fragment of DNA, but do so in an extremely accurate sequencing process. For such applications, shorter target segments may be employed, thus permitting a higher level of redundancy by sequencing multiple times around a small circular template, where such redundancy provides the desired accuracy. Thus, in some cases, the double stranded target segment may be much shorter, e.g., from 10 to 200, from 20 to 100 or from 20 to 50 or from 20 to 75 bases in length. For purposes of the foregoing, the length of the target segment in terms of bases denotes the length of one strand of the double stranded segment.

While different applications will have different impacts on the length of the target sequence portion that is included in the template molecule, the length and structure of the linking oligonucleotide or single stranded portions of the template may be dictated, at least in part, by structural considerations in addition to application specific criteria. In particular, at a minimum, the linking oligonucleotides are required to be able to form a connecting loop between the 3' end of one strand of a double stranded nucleic acid segment and the 5' end of the other strand. As such, where employed primarily as a linking oligonucleotides, e.g., without accommodating larger functional elements, the linking oligonucleotide typically will be from about 4 nucleotides to about 100 nucleotides or more, while linking oligonucleotides of from 4 nucleotides to about 20 nucleotides will be generally preferred. For example, where short linkages are desired, linking oligoucleotides may be from 4 to about 8 nucleotides in length.

In addition to the foregoing structural requirements, where a given linking oligonucleotide portion provides a primer and/or polymerase binding site, that segment must be of sufficient length to accommodate the desired primer length, as well as a complexed polymerase. Accordingly, linking oligonucleotides that include primer recognition sites will typically be greater than about 20 bases in length, and preferably at least about 36 bases in length. In some cases, it may be desirable to provide sufficient space on one or both sides of the primer within the single stranded portion, e.g., to accommodate polymerase binding, etc. As such, in some cases, the single stranded portion will be substantially greater than as set forth above, e.g., 50 bases, 80 bases, 100 bases or larger.

Notwithstanding the foregoing, in some cases, shorter linking oligonucleotides may be desirable, as templates with smaller hairpin loops show increased efficiency as templates in that less of the overall template construct, and thus, less of the sequencing capability of the system, is taken by the "overhead" of the linking oligonucleotides. Accordingly, linking oligonucleotides in some cases will be smaller than 20 bases in length, preferably smaller than 12 bases in length. As will be appreciated, where one desires to provide optimal primer binding, but enhanced efficiency, the linking oligonucleotides will generally be in the range of from about 20 to about 100 bases in length, preferably, from about 20 to about 80 bases in length. In addition, asymmetric linking oligonucleotides, e.g., having different numbers of nucleotides joining the sense and antisense strands, may be used within a single template construct. Such constructs could be generated through, e.g., iterative processes of cleavage of a sample segment with a first type of restriction endonuclease, followed by annealing/ligation of a first adapter/linking hairpin sequence that is complementary to the cleavage site/overhang sequence, followed by treatment with a second restriction endonuclease, followed by annealing/ligation with a second differently sized hairpin adapter, complementary to the second cleavage site/overhang.

V. Strand Displacement

As noted previously, the complementary segments of the template may be provided in double stranded form, e.g., as shown in FIG. 2B. As will be appreciated, in such cases, it will be preferable to affect strand separation either prior to or during the template dependent sequencing process. In the case of, for example, sequence by incorporation processes, strand separation is preferably carried out through the selection and use of a strand displacing polymerase enzyme. A variety of strand displacing polymerase enzymes are readily available, including, for example, Φ29 polymerase and Φ29 type polymerases (See, e.g., U.S. Pat. Nos. 5,001,050, 5,576,204, the full disclosures of which are incorporated herein by reference in their entirety for all purposes), Bst Polymerase (available from New England Biolabs), as well as those polymerases described in commonly owned International Patent Application Nos. WO 2007/075987, WO 2007/075873, WO 2007/076057 the full disclosures of which are incorporated herein by reference in their entirety for all purposes.

Figure 5:
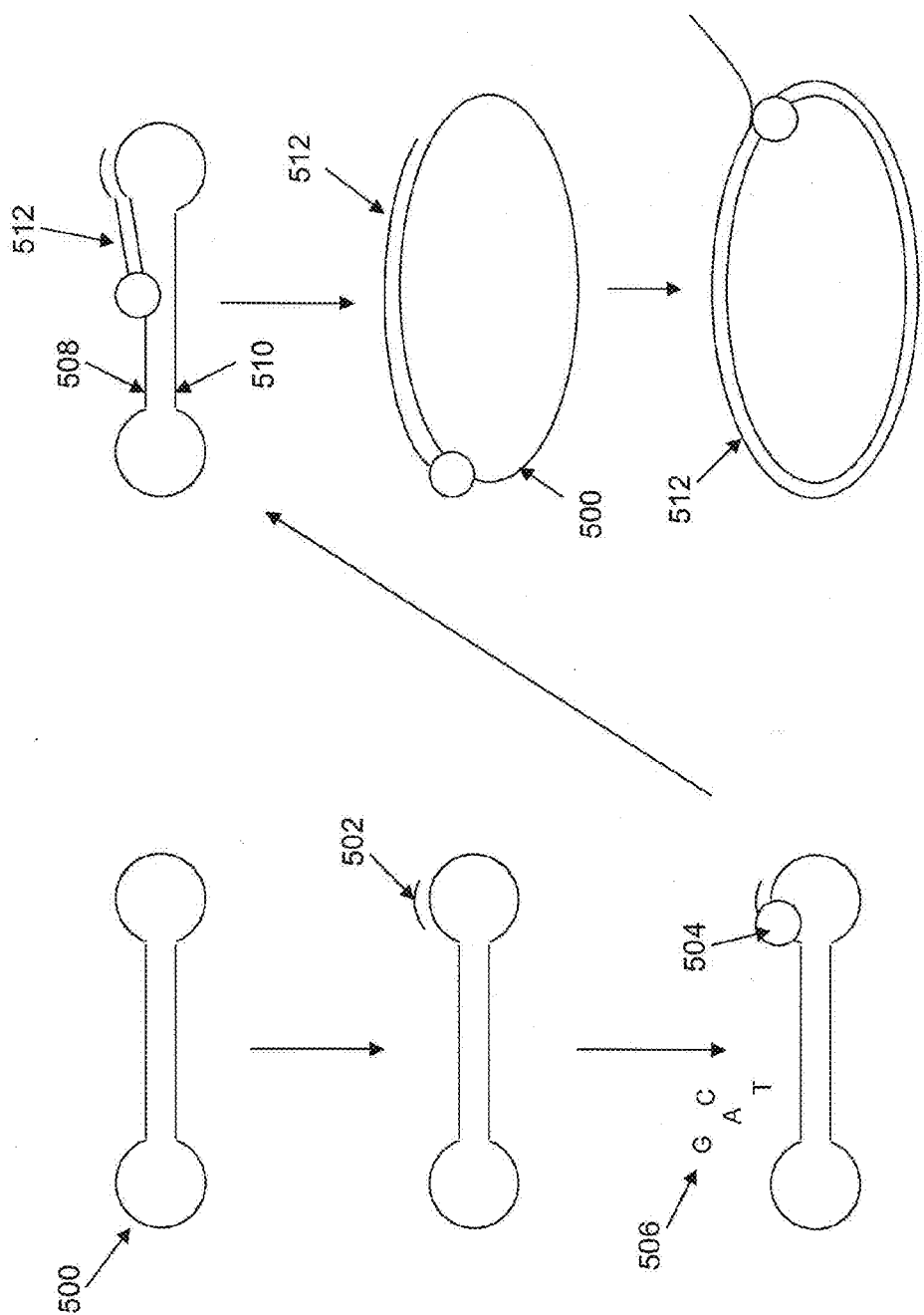
FIG. 5 schematically illustrates an overall consensus sequencing process using a template construct of the invention.

The synthesis process for such templates and strand displacing enzymes is schematically illustrated in FIG. 5. As shown, a completely contiguous template 500 is complexed with a primer sequence 502 and a strand displacing polymerase 504, and contacted with the four nucleotides 506, or in the case of certain preferred aspects, fluorescently labeled nucleotide analogs. As synthesis progresses, the polymerase's own activity displaces one complementary strand 508 from the other 510 and synthesis of the nascent strand 512 continues. Upon complete synthesis, e.g., one full cycle around the template, a double stranded circular sequence results, made up of the original template 500 and the newly synthesized or nascent strand 512. Because the strand displacing enzyme can continue to displace the hybridized strand, e.g., the newly synthesized nascent strand 512, the synthesis, and by implication, the sequencing process can continue through the template multiple times to provide multiple sequences for use in consensus sequence determination, typically generating a long, concatamer molecule containing repeated regions complementary to the contiguous template 500.

Alternatively, other mechanisms may be employed to affect strand separation prior to or during synthesis. For example, elevation of the temperature of the reaction mixture may be used to melt the double stranded portion of the template, and permit primer extension through that region. As will be appreciated, for such applications, it may be desirable to employ thermally stable polymerase enzymes that are better suited to the temperatures required for melting, and continued synthesis. A wide variety of thermostable polymerases are known in the art and are applicable to this type of application, including, for example Taq polymerase and its variants.

Figure 6:
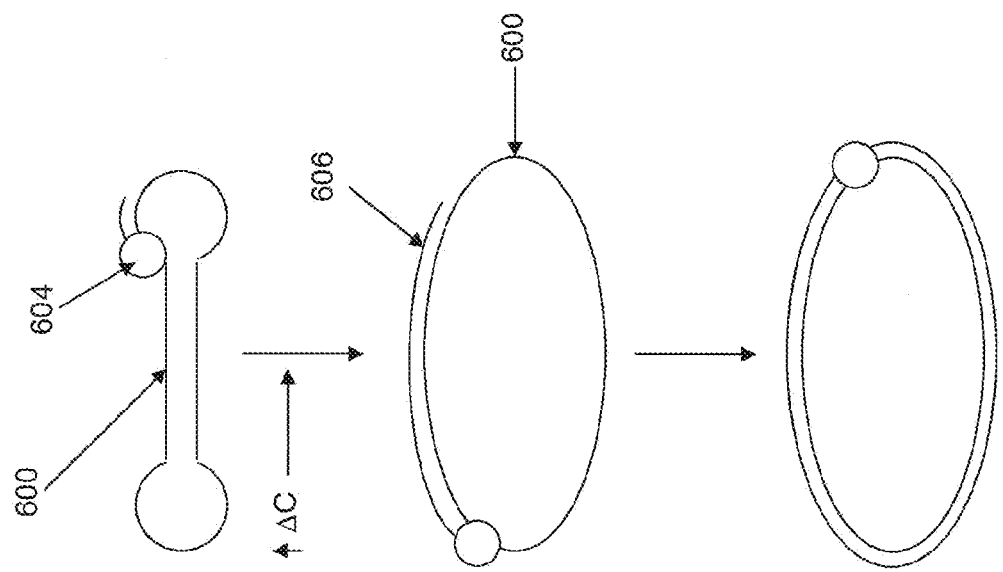
FIG. 6 schematically illustrates an alternative approach to a sequencing process using template constructs of the invention.

A schematic of synthesis using a thermally regulated initiation process is illustrated in FIG. 6. As shown, a primer 602 is tethered to the template structure 600 and contacted with the non-strand displacing polymerase enzyme 604. Because the template exists in a double stranded configuration and the polymerase is unable to displace the complementary strand, the synthesis does not readily proceed. At a desired point, the double stranded segment is separated to allow synthesis of the nascent strand 606 through the previously double stranded portion of the template 600, e.g., through heating sufficient to melt the double stranded segment without removing the primer (indicated as ΔC). As will be appreciated, primer sequences, as well as additional portions of the linking oligo-nucleotides, may be employed that have relatively higher melting temperatures, e.g., GC rich sequences, that have higher melting temperatures than an average naturally occurring nucleic acid sequence. Once the double stranded segment is duplicated sufficient to prevent re-hybridization of the original template, by virtue of the presence of the nascent strand, there is no longer a need for denaturation steps or additives.

As will also be appreciated, in the case of the use of non-strand displacing enzymes, additional strand separation steps will typically be needed following one complete cycle around the template, as the nascent strand would then be in position to block continued synthesis. As with initiation of the primer extension, the requirement for another triggering event can provide advantages of synchronizing different template sequence steps. Alternatively, following an initial triggering event, the synthesis reaction may be maintained at elevated temperatures to ensure continuous, uninterrupted synthesis and sequencing.

VI. Sequence Alignment

As alluded to above, and as an additional advantage, the template configurations of the invention have an inherent alignment potential for consensus sequence determination of the same or identical templates. In particular, because the connecting oligonucleotide is known or knowable, one can readily exploit this pre-known sequence in aligning long strings of sequence data from such template or templates, e.g., as a landmark or registration sequence. Further, even without knowledge of the sequence of the connecting oligonucleotide, one can derive the sequence by observing that portion of the overall sequence that does not possess a complementary portion elsewhere in the sequence data. In particular, the target sequence portion of the template, as a double stranded segment, will have, within the same sequence data, an internal complement, i.e., will have both a sense and an antisense strand. However, depending upon the length of the target segment and the connecting oligonucleotide, the probability of an exact complement to the connecting oligonucleotide existing within the target segment will be low to zero. As such, one can scan sequence data derived from a given template construct for a portion that has no internal complement elsewhere within the sequence, and assume this is the connecting oligonucleotide, and consequently, exploit it as an alignment marker.

One exemplary algorithm for accomplishing this would proceed as follows. First the entire sequence would be subjected to Smith-Waterman alignment with its own reverse complement. An alignment quality threshold would be applied so that the sequence would be annotated according to those regions that have an alignment with the reverse complement, and those that do not. The repeat unit of the sequence would be identified, e.g., using Fourier transform methods known in the art, or by application of the same Smith-Waterman algorithm of the sequence with itself rather than the reverse complement. The annotations from the first step are collapsed into a single repeat unit and summed. Then a more certain identification of the sequence insert can be made using the statistics of all of the repeats. For example, in 10 repeats, regions that show 1 or fewer hits against the reverse complement can be called "marker sequence" and regions that have 2 or more hits can be declared "genomic sequence". The precise thresholds can be determined by the needs of the application.

As alluded to above, however, the connecting or linking oligonucleotide may be selected or generated to include sequence with identifiable sequence characteristics to facilitate its identification, both with respect to the contiguous template sequence with which it is associated, and also with respect to other template sequences that may exist in the same sample mixture. In particular, one can utilize connecting oligonucleotides in the template constructs that include sequence markers like a barcode, to indicate the origin of a given template sample. Different template samples including distinguishable connecting oligonucleotide tags could then be pooled for analysis in a single sequencing process. Sequence data derived from individual templates is then attributable to the originating sample preparation process through the identification of the connecting oligonucleotide tag.

In particular, a number of discrete sample preparation processes are performed for different nucleic acid containing samples. These discrete sample preparation processes may be performed on different starting materials, e.g., different samples (cells, cell cultures, patients, etc.), different portions of the same original material, i.e., different size-selected portions or the like, or different portions of the same population, cell culture, etc. The template deriving from each discrete process is bar-coded through the use of a unique, identifiable and discrete linking nucleotide sequence in the template construct.

The different samples are then pooled for sequencing in a unified sequencing reaction. As the sequencing output from each run is based upon individual molecules, the sequencing data is then parsed out according to its origin by virtue of the barcode sequence that is integrated into the template molecules. In particular, because each sequence read is derived from a single molecule, the sequence of the insert portion of the template can be unambiguously linked to the sequence of its attached adapter sequence that includes the bar code sequence within that adapter sequence. Accordingly, each template sequence is then traced back to its origin, e.g., a particular sample, patient, etc.

VII. Contiguous Template Preparation

The template structures of the invention may be prepared in a number of different ways. In a first exemplary process, double stranded target fragments are coupled at one or both ends with separate hairpin loops to provide the template structures of the invention. Such methods provide simplified template preparation processes that reduce undesired concatamerization of fragments, and permit facile cleanup of random nucleic acid fragments from the preparation. For example, completely complementary double stranded nucleic acid fragments may be joined via blunt end ligation with hairpin adapter sequences. In such cases, given the reduced ability to control which adapter ligates to the different ends of the double stranded fragments, it may be desirable to employ a single type of adapter. Such completely complementary double stranded segments may be generated using blunt end cutting enzymes, or through the use of restriction enzymes that yield overhangs, followed by filling in of the overhanging single strands, e.g., using Klenow fragment or the like.

In other methods, described herein, ligation processes may be employed that controllably ligate a given adapter type to a given end of the double stranded fragment, thus allowing the use of identifiable sequences within the linking oligonucleotides, to facilitate identification of one end of the template from the other.

Figure 7:
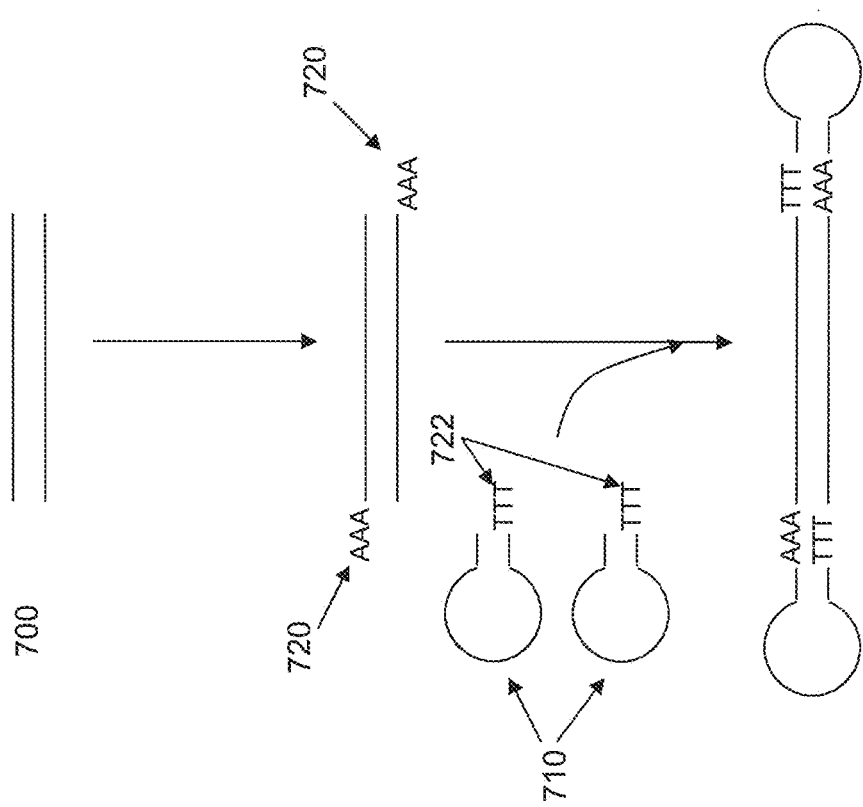
FIG. 7 schematically illustrates an exemplary assembly process of the template constructs used in the invention.

One of such methods is schematically illustrated in FIG. 7. As shown, a double-stranded nucleic acid fragment or fragments, e.g., double stranded fragment 700, is provided. The double stranded fragment may be derived from the fragmentation of larger target nucleic acids, e.g., genomic DNA, cDNA, DNA concatamers, and/or amplification products, e.g., from PCR or LCR amplification, or the like. Hairpin adapters 710 are then appended to each end of the double stranded fragment 600. As shown, the attachment of the hairpin adapters 710 relies upon the presence of unique overhang sequences 720 at the 3' end of each strand of the double stranded fragment 700. Complementary overhang sequences 722 are provided on the hairpin adapters, to provide for specific annealing and ligation of the hairpin adapters 710 to the double stranded fragments 700. As shown, the overhang sequences are the product of A-tailing of the double stranded fragment which appends a series of adenosine nucleotides to the 3' end of each strand. A complementary set of thymidines at the 3' end of each of the hairpin adapters provides for specific annealing. However, a number of different specific overhang sequences may be provided at the ends of the double stranded fragments. For example, restriction endonucleoases may be used to fragment a larger segment of double stranded DNA leaving a characteristic overhang sequence at every cleavage point. The complementary sequence to this characteristic sequence is then provided upon the hairpin adapter to provide specific annealing and ligation. Alternatively, specific overhang sequences may be separately ligated to the 3' or 5' ends of each strand for use as the overhang sequence. In addition to providing specificity for hairpin annealing, the overhang sequences also serve to prevent concatamerization of the fragments prior to annealing and ligation of the hairpin adapters. Following annealing, the hairpin adapters are ligated to the fragments, using standard ligation processes.

As noted above, while less preferred for its lack of additional specificity and other advantages, blunt end ligation also may be employed in ligating hairpin adapters to the ends of the double stranded fragments. In such cases, concatamerization of the template fragments or other non-specific associations may be avoided through the use of excess amounts of hairpin adapters. Alternatively, emulsion based reactions, where individual droplets within the emulsion are sized substantially to provide individual molecules, may provide protections against concatamerization.

In an alterative process, a template sequence may be formed using an alternate ligation process to form the template configuration provided herein. In some cases, this alternate ligation process may incorporate exogenous linking segments, e.g., not part of the original target sequence, while in other instances; portions of the original target nucleic acid may be used to form the linking oligonucleotides. In the case of internal sequences used as the linking oligonucleotides, such sequences may derive from single stranded overhang sequences, or may be derived from a double stranded portion of a blunt ended fragment.

In either event, covalent linkage of adjacent 3' and 5' ends of a double stranded nucleic acid segment, whether from the original target segment, or as a result of an appended or ligated exogenous linking oligonucleotide sequence, may be carried out using, e.g., a template independent, dsDNA end (TIDE) ligation process, using, for example a circligase enzyme system. Typically, this process will require the presence of a phosphate group at the 5' end of each segment in order to permit circligase action. Addition of the 5' phosphate may be accomplished upon the fragment enzymatically, e.g., using a T4 polynucleotide kinase, or the like. Alternatively, where the double stranded segment was synthesized, or created from another template, rather than from the fragmenting of a larger nucleic acid, the phosphorylated 5' terminus could be provided during the synthesis process, e.g., on a primer sequence used for amplification of the original target sequence, as an initial building block in solid phase synthesis, or the like.

Figure 8:
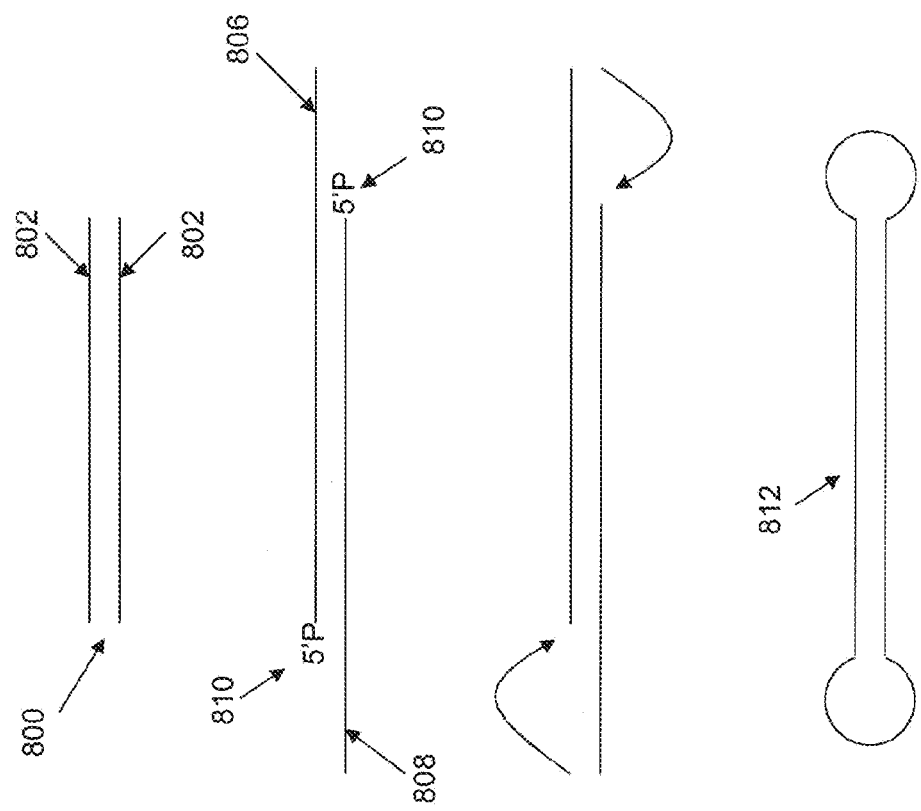
FIG. 8 schematically illustrates an alternate assembly process for template constructs.

FIG. 8 schematically illustrates an exemplary process for coupling the 3' and 5' ends of a double stranded fragment. As shown, a double stranded fragment 800 of a target sequence is provided, that is comprised of strands 802 and 804. Overhang sequences 806 and 808 are provided on the double stranded segment 802 and 804, respectively. Such overhang sequences may be added to the fragments using by a variety of methods, e.g., using standard tailing techniques, such as treatment with terminal transferases to add poly-A tails, ligating adapter sequences to the target fragments that contain such overhang sequences, or the like. Also, although shown as sequences added to the double stranded fragment, it will be appreciated that such overhang sequences may be provided during the fragmentation process, e.g., as overhang sequences from, e.g., restriction endonuclease digestion of larger nucleic acids.

As shown, a 5' phosphate group 810 is coupled to each strand to permit TIDE ligation and closure of the two adjacent ends. Upon treatment with a ligase having appropriate closure activity, e.g., Circligase ssDNA ligase (Epicentre Biotechnologies, Madison Wis.), T4 RNA ligase, or the like each end of the double stranded target is closed to provide a completely contiguous template sequence 812 of the invention.

Demonstration of the joining of a 5' phosphated nucleotide to a 3' hydroxyl of double stranded nucleic acid fragments employed a commercial Circligase enzyme system, but with additional modifications to the protocol (addition of 5' phosphate, presence of $MnCl_2$, ATP and a reaction temperature of 60° C. for greater than 1 hour). The resulting molecule was resistant to exonuclease digestion (by both exonuclease I and exonuclease III) as monitored by PAGE, indicating that the resulting molecule was closed on both ends.

An alternative process for providing overhang sequences for the foregoing process employs blocked primer sets in an amplification process to generate double stranded nucleic acid segments that retain overhang sequences. In particular, amplification primer pairs are provided to amplify a segment of double stranded DNA, e.g., they prime opposing ends of complementary strands of the targeted segment for antiparallel amplification. The primer pairs are configured to be partially complementary to the target segment, and have within their sequence, one or more non-native nucleotides (referred to herein as a "$5^{th}$ base"). Inclusion of the fifth base within the primer sequence, for which no complements are provided in the amplification mix, will prevent the target sequence from extending the target along the primer sequence, and thus, retain the single stranded overhang sequence in the resulting double stranded product. Likewise, repeated cycles of amplification will result in the vast majority, and approaching substantially all, of the amplification product having the overhang sequence retained on both strands of the double stranded product. These double stranded segments may then be used in the template generation processes described herein.

Figure 9:
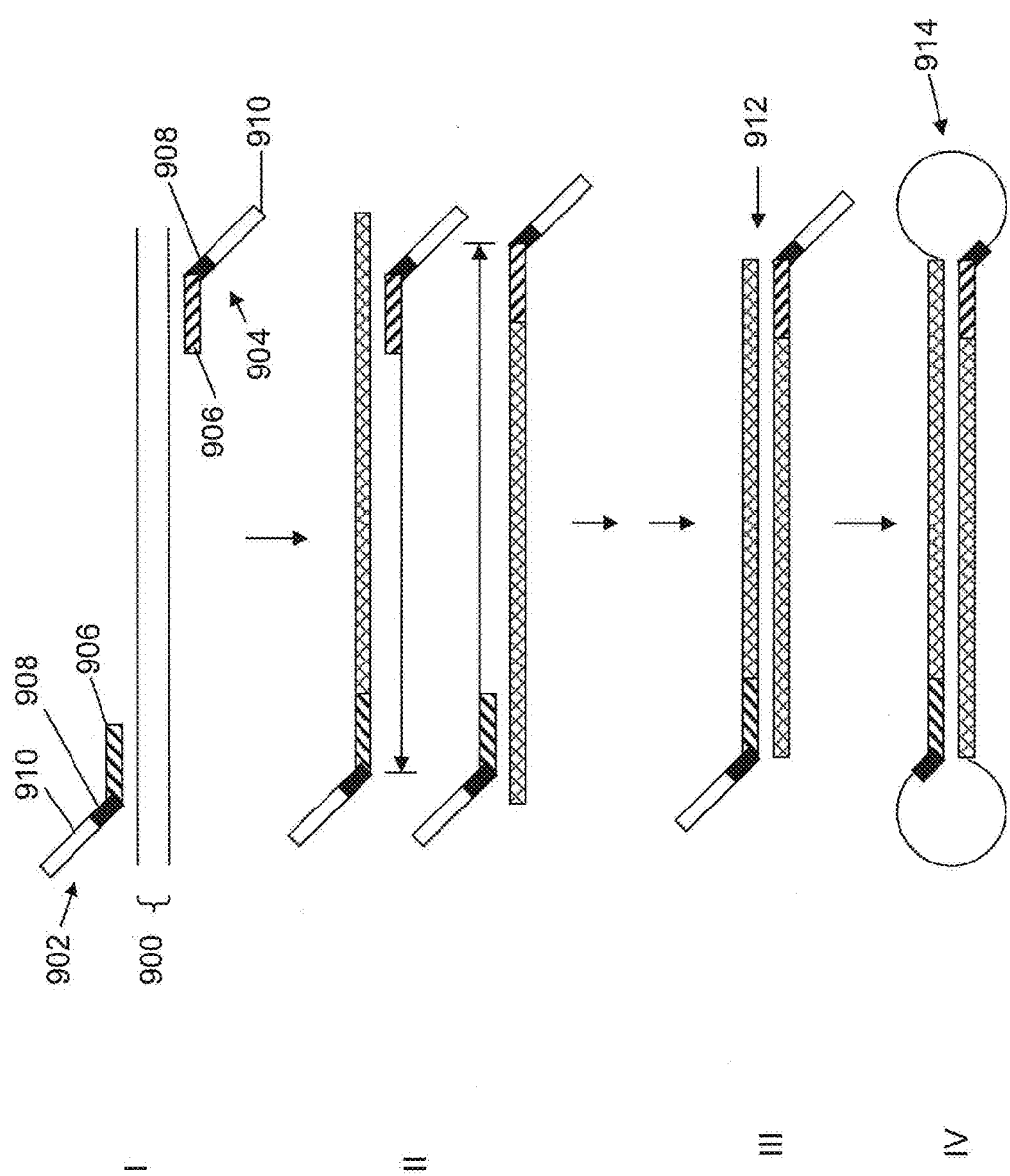
FIG. 9 schematically illustrates another template preparation process of the invention.

A schematic illustration of an example of the foregoing process is provided in FIG. 9. As shown, a double stranded target nucleic acid segment 900, is anti-parallel primed using primers 902 and 904 (Panel I). As shown, each primer includes a first portion 906, that is complementary to its strand of the target sequence 900, a second portion 908 that includes one or more non-native nucleotides or $5^{th}$ bases, and a third portion 910, which, as shown, is non-complementary to the target segment 900. Although shown as being non-complementary, this is not required for operability of the process. In some cases, for example, use of complementary third portions 910, may provide higher affinity of the primers to the desired target segments by virtue of the primer having two segments that are complementary to the desired segment, and less likelihood of binding to non target regions, where the $5^{th}$ base portions do not excessively interfere with hybridization of both the first and third portions to the target segment. The primers are extended in a standard amplification process, e.g., PCR, but in the absence of the complement of the $5^{th}$ base.

As shown by the arrows in panel II, primer extension against each amplification product will terminate at the same position, i.e., the position complementary to the $5^{th}$ base in the complementary strand. Following multiple rounds of amplification (Panel III), the amplification product will be substantially made up of complementary strands having overhang sequences that contain the $5^{th}$ base containing portion (second portion 908) and the third portion of the primer (910), that can be annealed to provide double stranded nucleic acids 912.

The double stranded nucleic acids 912, having overhang sequences on the 5' end of each segment, are then subjected to the ligation processes described above (and illustrated in Panel IV), to provide contiguous templates 914 of the invention.

As will be appreciated, the primer sequences may be separately synthesized and configured to include those functional groups necessary and/or desirable for the ligation process. For example, such primers may be synthesized to include the 5' phosphate group used in a TIDE ligation process. Additionally, they may be synthesized to include, e.g., within third portion 910, a sequencing priming site, e.g., different from the amplification priming site in portion 906, or other functional sequence, as set forth elsewhere herein. In addition, the presence of the $5^{th}$ base portion, e.g., one or more non-native bases in the linking oligonucleotide portion of a resulting contiguous template construct, can provide yet another indicator and/or control sequence or sequence event outside of the double stranded segment of the target sequence. Alternatively, the region 910 could also be partially self-complimentary to form a stem-loop structure, placing the 5' end adjacent to the 3'-end of the blocked extension. This could then potentially be used as a substrate for a more standard T4 DNA ligase mediated method, e.g., as described above.

By way of example, a sequencing reaction may be initiated in the absence of the complement to the $5^{th}$ base. Because this is a non-native base, it's absence will not impact the overall sequence determination of the target portion for the sequence. However, by starving the reaction for this complement, one can prohibit synthesis, and thus, the sequencing process, until the $5^{th}$ base complement is added to the mixture, providing a hot start capability for the system. Additionally, as a non-native base, this portion of the overall template construct provides an internal check on sequencing process and progress that is configurable to not interfere with sequence analysis of the native bases in the template. For example, the $5^{th}$ base complement in the sequence mixture may be provided with a wholly detectably different label than the complements to the four native bases in the sequence. The production of incorporation based signals associated with such labels then provides an indication that the process is about to start processing one strand of the target nucleic acid. Likewise, it can provide a clocking function for the number of times the process has proceeded around a completely contiguous template. Although described as the "$5^{th}$ base" it will be appreciated that this may comprise a set of non-natural bases that can provide multiple control elements within the template structure. For example, two different non-native or $5^{th}$ bases could be included within the template structure, but at different points, to regulate procession of the sequencing process, e.g., allowing controlled initiation, and a controlled stop/start, later in the sequence, e.g., prior to sequencing the antisense strand. For example, one could add the complement to the first non-native base in order to initiate sequencing. Upon encountering the second non-native base, e.g., at the first hairpin turn, sequencing would stop in all reactions, until the complement to that second base was added to the reaction mixture. This would allow a resynchronization of the various sequencing reactions, and or an ability to control sequencing the opposing strand, providing a paired end sequencing configuration as discussed elsewhere herein.

Figure 10:
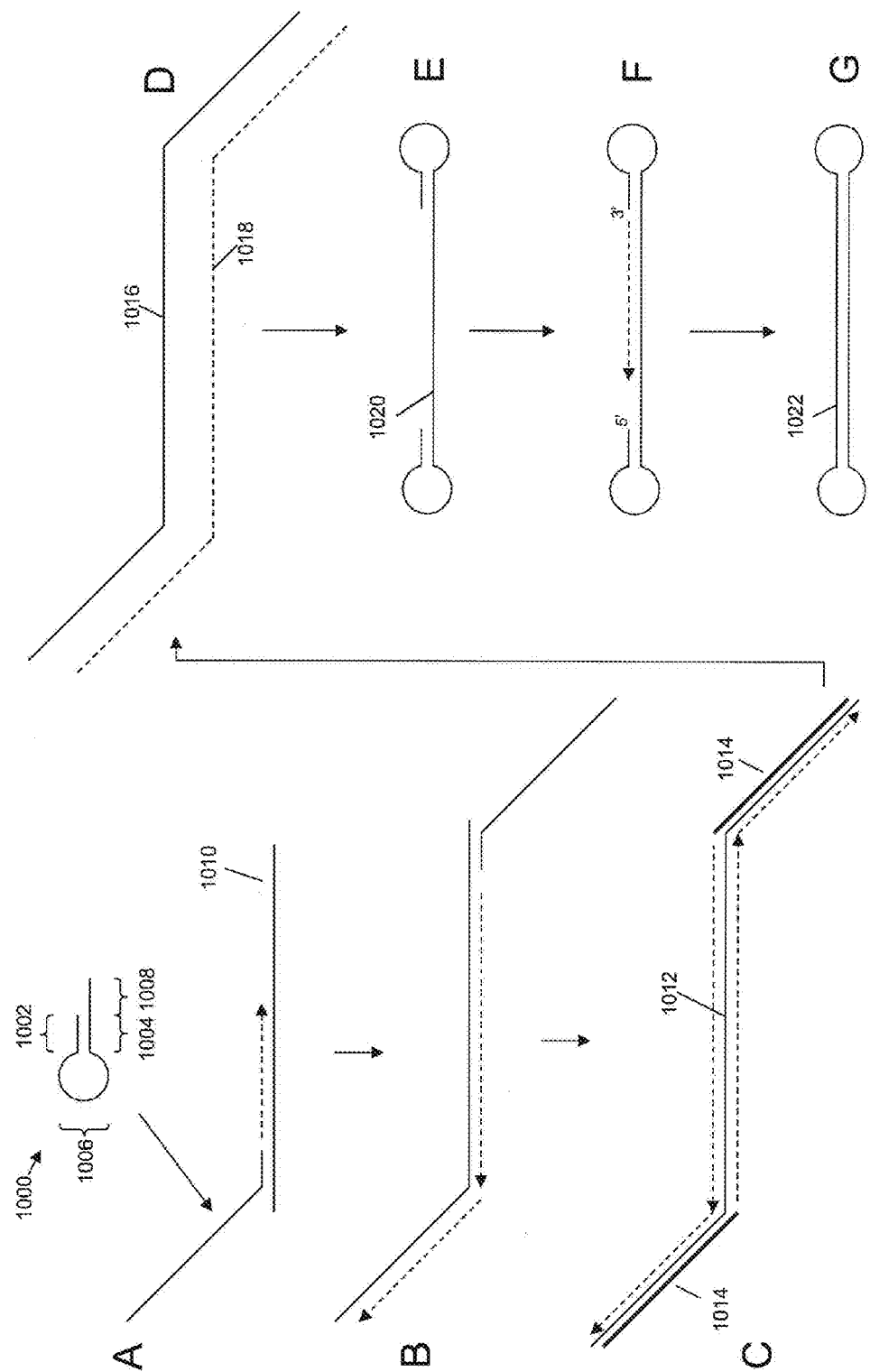
FIGS. 10A-G schematically illustrate an alternate template preparation process according to the invention.

A similar or related process for preparing either partially or completely contiguous template constructs is illustrated in FIG. 10. In particular, as shown, a first amplification primer sequence 1000 is provided that includes first and second complementary segments 1002 and 1004, respectively, linked by a linking oligonucleotide 1006, e.g., as described elsewhere herein. In addition, a single stranded target priming segment 1008 is provided at the 3' end of the overall amplification primer. In some cases, the target priming segment 1008 may be specifically selected to prime adjacent to or within desired sequence locations. In other preferred aspects, the target priming segment will randomly prime within a given genome or other large DNA sequence to ensure optimal coverage in generating template libraries for sequencing. By way of example, in the case of random priming, the target priming segment 1008 may be comprised of relatively small oligonucleotides, e.g., hexamers, heptamers, octamers, or the like. For more specific priming, the target priming segment will typically comprise larger segments on the order of 16, 20 or more nucleotides within the target priming segment. Additionally, such segments will typically comprise a sequence complementary to a known sequence segment adjacent to or otherwise proximal to a desired target sequence.

As shown in FIG. 10, the first amplification primer 1000 is denatured and allowed to hybridize to a target nucleic acid segment 1010. In some cases, the primer 1000 is configured to be denatured under conditions which still allow it to anneal to the target sequence 1010. In other cases, the structure of the primer will permit hybridization and priming of the target segment 1010, even when the primer is in its hairpin structure, e.g., without denaturation.

By way of example, and as shown, at step A, the reaction mixture is heated to an appropriate denaturing temperature for the first amplification primer 1000, e.g., 37° C., and the primer is allowed to anneal to the target segment 1010. As shown, isothermal amplification of the target segment 1010 is then carried out (Steps A and B) to generate further amplifiable target segments having the hairpin structure of the first amplification primer appended to each end (Segment 1012 in Step C). Note that although illustrated as a single line in FIG. 10, it will be appreciated that for purposes of discussion, the single illustrated line illustrating the target segment 1010 and amplifiable target segments 1012 represents either one or both of the sense and antisense strands of a complementary nucleic acid.

This segment is then subjected to geometric amplification, e.g., PCR, using second amplification primers 1014 against the initial amplification primer sequence 1000, e.g., complementary to one or more of segments 1002, 1004, 1006 and even 1008, or their complements, to yield amplification products, e.g., complementary template segments 1016 and 1018. Following the amplification of segment 1012 (Step E), renaturation of the original first amplification primer segments, or the partially overlapping isothermal or PCR amplification primer segments or their complements within the amplification product, e.g., 1016, results in the formation of hairpin structures at each end of the amplification products (Step E) to form partially double stranded partially contiguous nucleic acid segments 1020. These partially double stranded segments 1020 are then converted (Step F and G) to completely contiguous segments 1022, by subjecting the self priming partially double stranded segments to 3' extension, e.g., using non-strand displacing nucleic acid polymerases, e.g., Klenow fragment, followed by ligase treatment to couple the resulting 3' terminus to the 5'end. Following ligation, the amplification mixture is then subjected to exonuclease digestion to remove any nucleic acid segments that are not fully contiguous, e.g., were either not ligated or not fully extended.

Although the constructs of the invention are described primarily, and preferably, for use directly as templates for, e.g., sequencing applications, it will be appreciated that these structures may also serve as intermediate structures in the preparation of templates that provide for sequence redundancy in line with that provided by such constructs. For example, the structurally circular nucleic acid segments described herein, may be used as templates in a rolling circle replication process to produce concatamer molecules that include repeating copies of both the sense and antisense strands of the originating double stranded segment included within the circular nucleic acid. These replicated products may then be employed directly as template molecules in a template dependent sequencing process, as described elsewhere herein (See also U.S. Pat. No. 7,476,503, which is incorporated herein by reference in its entirety for all purposes). Likewise, duplication processes may be employed to produce multiple copies of a prepared circular construct using methods previously described (See, e.g., U.S. Patent Application No. 61/072,160, previously incorporated herein by reference in its entirety for all purposes).

Generation of the double stranded nucleic acid segments that are used in the preparation of the template constructs of the invention may be accomplished by a number of means. For example, nucleic acids derived from samples to be analyzed may be fragmented into double stranded fragments through known fragmentation methods, e.g., as noted below. Alternatively, double stranded templates may be generated from targeted regions of the sample nucleic acid segments through bidirectional amplification of desired sequence segments within a larger sequence. In particular, one can employ sequence specific PCR primers on flanking portions of a desired sequence region to amplify the region bounded by the primers through antiparallel amplification, either alone, or in conjunction with an initial linear amplification process. The resulting amplified product includes the double stranded sequence region of interest, which is then subjected to additional processing to yield the template constructs of the invention.

As described above, the template nucleic acids of the invention that are provided by the methods described herein, e.g., for use in single molecule sequencing reactions, can be derived from a genomic DNA. Genomic DNA can be prepared from any source by three steps: cell lysis, deproteinization and recovery of DNA. These steps are adapted to the demands of the application, the requested yield, purity and molecular weight of the DNA, and the amount and history of the source. Further details regarding the isolation of genomic DNA can be found in Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2008 ("Sambrook"); Current Protocols in Molecular Biology, F. M. Ausubel et al., eds., Current Protocols, a joint venture between Greene Publishing Associates, Inc. and John Wiley & Sons, Inc ("Ausubel"); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley). In addition, many kits are commercially available for the purification of genomic DNA from cells, including Wizard™ Genomic DNA Purification Kit, available from Promega; Aqua Pure™ Genomic DNA Isolation Kit, available from BioRad; Easy-DNA™ Kit, available from Invitrogen; and DnEasy™ Tissue Kit, which is available from Qiagen. Alternatively, or additionally, target nucleoc acid segments may be obtained through targeted capture protocols where target nucleic acids are obtained initially as single stranded segments on microarrays or other capture techniques, followed by amplification of the captured material to generate double stranded sample materials. A variety of such capture protocols have been described in, e.g., Hodges E, et al. Nat. Genet. 2007 Nov. 4, Olson M., Nature Methods 2007 November; 4(11): 891-2, Albert T J, et al. Nature Methods 2007 November; 4(11):903-5, and Okou D T, et al. Nature Methods 2007 November; 4(11):907-9.

The nucleic acids that can be prepared by the methods described herein, e.g., for use with high-throughput sequencing systems can also be derived from a cDNA, e.g. cDNAs prepared from mRNA obtained from, e.g., a eukaryotic subject or a specific tissue derived from a eukaryotic subject. Data obtained from sequencing the nucleic acid templates derived from a cDNA library, e.g., using a high-throughput sequencing system, can be useful in identifying, e.g., novel splice variants of a gene of interest or in comparing the differential expression of, e.g., splice isoforms of a gene of interest, e.g., between different tissue types, between different treatments to the same tissue type or between different developmental stages of the same tissue type.

mRNA can typically be isolated from almost any source using protocols and methods described in, e.g., Sambrook and Ausubel. The yield and quality of the isolated mRNA can depend on, e.g., how a tissue is stored prior to RNA extraction, the means by which the tissue is disrupted during RNA extraction, or on the type of tissue from which the RNA is extracted. RNA isolation protocols can be optimized accordingly. Many mRNA isolation kits are commercially available, e.g., the mRNA-ONLY™ Prokaryotic mRNA Isolation Kit and the mRNA-ONLY™ Eukaryotic mRNA Isolation Kit (Epicentre Biotechnologies), the FastTrack 2.0 mRNA Isolation Kit (Invitrogen), and the Easy-mRNA Kit (BioChain). In addition, mRNA from various sources, e.g., bovine, mouse, and human, and tissues, e.g. brain, blood, and heart, is commercially available from, e.g., BioChain (Hayward, Calif.), Ambion (Austin, Tex.), and Clontech (Mountainview, Calif.).

Once the purified mRNA is recovered, reverse transcriptase is used to generate cDNAs from the mRNA templates. Methods and protocols for the production of cDNA from mRNAs, e.g., harvested from prokaryotes as well as eukaryotes, are elaborated in *cDNA Library Protocols*, I. G. Cowell, et al., eds., Humana Press, New Jersey, 1997, Sambrook and Ausubel. In addition, many kits are commercially available for the preparation of cDNA, including the Cells-to-cDNA™ II Kit (Ambion), the RETROscript™ Kit (Ambion), the CloneMiner™ cDNA Library Construction Kit (Invitrogen), and the Universal RiboClone® cDNA Synthesis System (Promega). Many companies, e.g., Agencourt Bioscience and Clontech, offer cDNA synthesis services.

In some embodiments of the invention described herein, nucleic acid fragments are generated from a genomic DNA or a cDNA. There exist a plethora of ways of generating nucleic acid fragments from a genomic DNA, a cDNA, or a DNA concatamer. These include, but are not limited to, mechanical methods, such as sonication, mechanical shearing, nebulization, hydroshearing, and the like; chemical methods, such as treatment with hydroxyl radicals, Cu(II): thiol combinations, diazonium salts, and the like; enzymatic methods, such as exonuclease digestion, restriction endonuclease digestion, and the like; and electrochemical cleavage. These methods are further explicated in Sambrook and Ausubel.

VIII. Kits and Systems

In addition to the template compositions described above, and methods of making and using such compositions, the present invention also provides applied embodiments of such methods and compositions.

For example, in certain embodiments, the present invention provides kits that are used in preparation and use of the template constructs of the invention. A first exemplary kit provides the materials and methods for preparation of the template constructs in accordance with the invention, as described elsewhere herein. As such, the kit will typically include those materials that are required to prepare template constructs as outlined herein, e.g., in accordance with the various template preparation processes outlined above. As will be appreciated, depending upon the nature of the template construct, and the method used, the kit contents can vary. For example, where one is employing hairpin adapters that are coupled to the ends of double stranded nucleic acid segments, the kits of the invention will typically include such hairpin adapters, along with appropriate ligation enzymes and protocols for attaching such adapters to the free ends of double stranded nucleic acids, as well as any processing enzymes that may be desirable for treating the ends of the double stranded segments prior to ligation, e.g., to provide overhangs or blunt end nucleic acids. As noted previously, such adapters may include overhang segments to facilitate coupling to complementary overhang ends on the double stranded segment. These overhang ends may be the result of a known added sequence to the double stranded segment, e.g., resulting from restriction enzyme cleavage, tailing processes, or the like, and the reagents for preparing templates having these characterisrtics may optionally be provided within the kits or they may be obtained from commercial sources.

In other embodiments, these kits may include primers or other sequence adapters or sequence extension reagents for providing overhang sequences that may be used to provide linking oligonucleotides between the two strands of the double stranded nucleic acid segment. In some cases, these kits may include enzyme systems for providing 5' phosphate groups to the linking oligonucleotides, or may provide amplification primers that have such 5' phosphate groups predisposed upon the primers. Such primers may additionally include the $5^{th}$ base configurations set forth above, for controlling both the amplification process as well as the use of the resulting templates in sequencing applications.

A second exemplary kit provides materials and methods not just for the preparation of the template constructs of the invention, but also for the use of such templates in performing sequence analysis on target nucleic acid sequences. Thus, in addition to the materials and methods set forth above, such kits may additionally include reagents used in such sequencing processes, such as primer sequences for initiating the sequence process, polymerase enzymes, and in preferred cases, substrates that provide for optical confinement of nucleic acid synthesis complexes. In particularly preferred aspects, such substrates will typically include one or more arrays of zero mode waveguides. Such waveguide arrays may further include surface treatments that provide for enhanced localization of synthesis complexes within the illumination volumes of such zero mode waveguides, e.g., as described in Published International Patent Application No. WO 20071123763, incorporated herein by reference in its entirety for all purposes. Additionally, such kits may optionally include nucleotide compositions for use in sequencing applications, including, for example labeled nucleotides that include fluorescent or otherwise detectable labeling groups coupled to the phosphate groups in a nucleoside polyphosphate construct at a phosphate group other than the alpha phosphate. A variety of other types of labeled and unlabeled nucleotides may be optionally includes within the kits and are generally known in the art.

The invention also provides systems that are used in conjunction with the template constructs of the invention in order to provide for analysis of target nucleic acid molecules. In particular, such systems typically include the reagent systems described herein, in conjunction with an analytical system for detecting sequence information from those reagent systems. For example, depending upon the nature of the sequencing process employed, the sequencing systems may include the system components provided with or sold for use with commercially available nucleic acid sequencing systems, such as the Genome Analyzer System available from Illumina, Inc., the GS FLX System, available from 454 Life Sciences, or the ABI 3730 System available from Life Technologies, Inc.

In preferred aspects, such systems include fluorescence microscopes capable of resolving fluorescent signals from individual sequencing complexes. In particularly preferred aspects, such systems include arrays of reaction regions, e.g, zero mode waveguide arrays, that are illuminated by the system, in order to detect fluorescent signals therefrom, that are in conjunction with sequencing reactions being carried out within each ZMW.

The systems of the invention also typically include information processors or computers operably coupled to the detection portions of the systems, in order to store the signal data generated by the system (e.g., the sequencing reactions incorporating labeled nucleotides which are illuminated in the system and thereby produce fluorescent signals indicative of such incorporation) obtained from the detector(s) on a computer readable medium, e.g., hard disk, CD, DVD or other optical medium, flash memory device, or the like. For purposes of this aspect of the invention, such operable connection provide for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (See, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007, now abandoned, and U.S. patent application Ser. No. 12/134,186, filed Jun. 5, 2008, now U.S. Pat. No. 8,182,993, the full disclosures of which are incorporated herein by reference in their entirety for all purposes.

IX. Examples

The template constructs described herein were employed in various sequencing applications which are described in greater detail, below.

Example 1

Template Construction and Sequencing

Template constructs in accordance with the invention were prepared for use in a sequencing by incorporation context. In particular, the template was subjected to single molecule real time (SMRT™) sequencing in which the polymerase mediated, template dependent extension of a primer sequence was monitored as labeled nucleotide analogs were being used for incorporation into the resulting nascent strand.

Template Construction:

A double-stranded fragment of DNA was amplified from a plasmid clone using primers 5'-GTACGGGTCTCAC-CCGGGGATCCTCTAGAATCGAT-3' (SEQ ID NO:1) and 5'-CCTAAGGTCTCGGAAGCTACTAGTCCTCAG-CAAGCTT-3' (SEQ ID NO:2). The resulting product was purified using a Zymo-25 PCR purification kit. Overhangs were generated on each end of the PCR product by incubating overnight in the presence of the restriction enzyme BsaI (NEB). The digested product was purified using a Qiagen PCR purification kit, and then ligated to the synthetic hairpin oligos: 5'-CGGGCTCGGAACGAAAGTTCCGAG-3' (SEQ ID NO:3) and 5'-CTTCGGTCGCCAGATTA-GAAAATCAGTCACGTCTAGATGCAGTCAGGTTCT-TAAATCCT AGTTCCTTGGCGACC-3' (SEQ ID NO:4). Ligation was performed by incubating the digested PCR product with a 2-fold excess of each hairpin oligo in the presence of T4 DNA Ligase (NEB) at 23° C. for one hour. Non-ligated products were removed by incubating the reaction in the presence of Exonuclease III for 1 hour at 37° C.

The final product was purified using a Qiagen PCR Purification Kit, and annealed to an equimolar amount of sequencing primer: 5'-CTGACTGCATCTAGACGTGACTGA-3' (SEQ ID NO:5). The final template construct included a 244 nucleotide duplex segment and an overall length of 546 nucleotides (including linking/hairpin segments).

The SMRT™ sequencing reaction was carried out with 2 nM DNA polymerase; 100 nM template; 500 nM A647-dA6P, 500 nM A660-dC6P, 500 nM A568-dG6P, and 500 nM A555-dT6P; Trolox at 0.5 mM; PCA (protocatechuic acid) at 4 mM; and PCD (protocatechuate 3,4 dioxygenase) at 0.5×.

Figure 11:
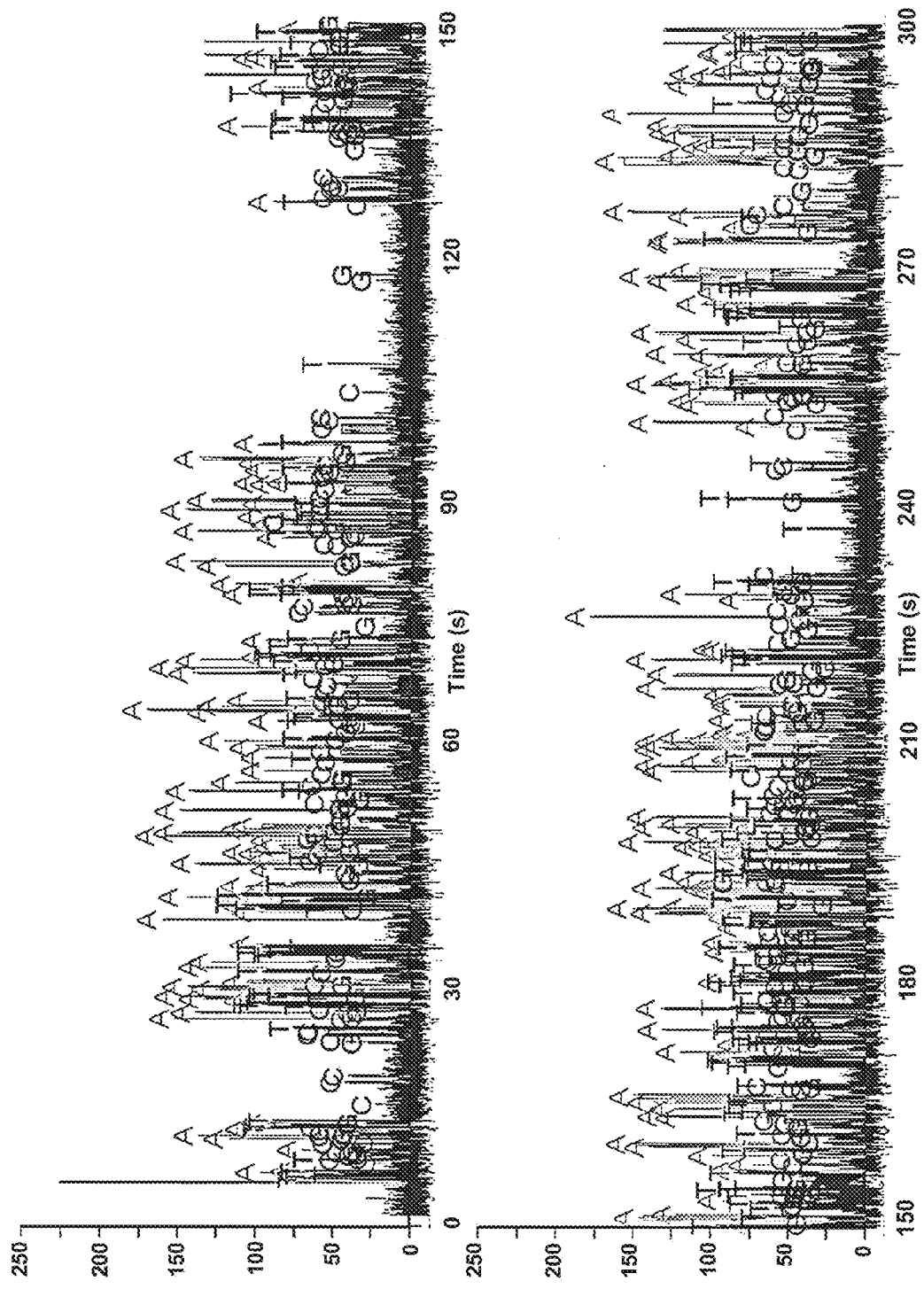
FIG. 11 provides sequence readout from a template construct of the invention.

The sequencing reaction was carried out in a zero mode waveguide array having 3000 discrete cores of the ZMWs. The reaction was observed using a highly multiplexed confocal fluorescent microscope providing a targeted illumination profile, e.g., a separate spot for each core (See, e.g., U.S. patent application Ser. No. 12/151,979, filed May 9, 2008, now U.S. Pat. No. 7,714,303, which is incorporated herein by reference in its entirety for all purposes). Fluorescent signals from the various ZMWs were detected on an EMCCD camera for 5 minutes, and were subjected to pulse recognition and base calling processes (See, e.g., Published U.S. Patent Application No. 2009-0024331, and incorporated herein by reference in its entirety for all purposes). FIG. 11 shows a sequencing trace showing 700 bases of sequence data around the template construct providing 154 bases of consensus information.

Example 2

Single Molecular Consensus Sequencing

Single molecular consensus sequencing accuracy was assessed using the template constructs of the invention. A completely contiguous SMRTbell™ template was generated containing 162 nucleotides total. In generating the contiguous template, two hairpin sequences were used. The first contained a 54 nt loop closed with an 8 bp stem and a 4 nt overhang that is used to ligate to an overhang present in the insert oligonucleotides. The second consisted of a 4 nt loop closed with an 8 bp stem and a 4 nt overhang for ligation. When sequenced in a single molecule sequencing system, each strand of this template can be sequenced multiple times. The resulting template was subjected to SMRT™ Sequencing as described above, which iteratively sequenced the template in a single molecule configuration, multiple times. Individual iterative sequence reads of a single template molecule showed increasing accuracy over multiple reads, as was expected. In particular, the accuracy obtained from repeatedly sequencing the single template molecule increased with each iterative sequence read or "loop", and approaching the asymptotic maximum after only several complete loops around the template.

Figure 12:
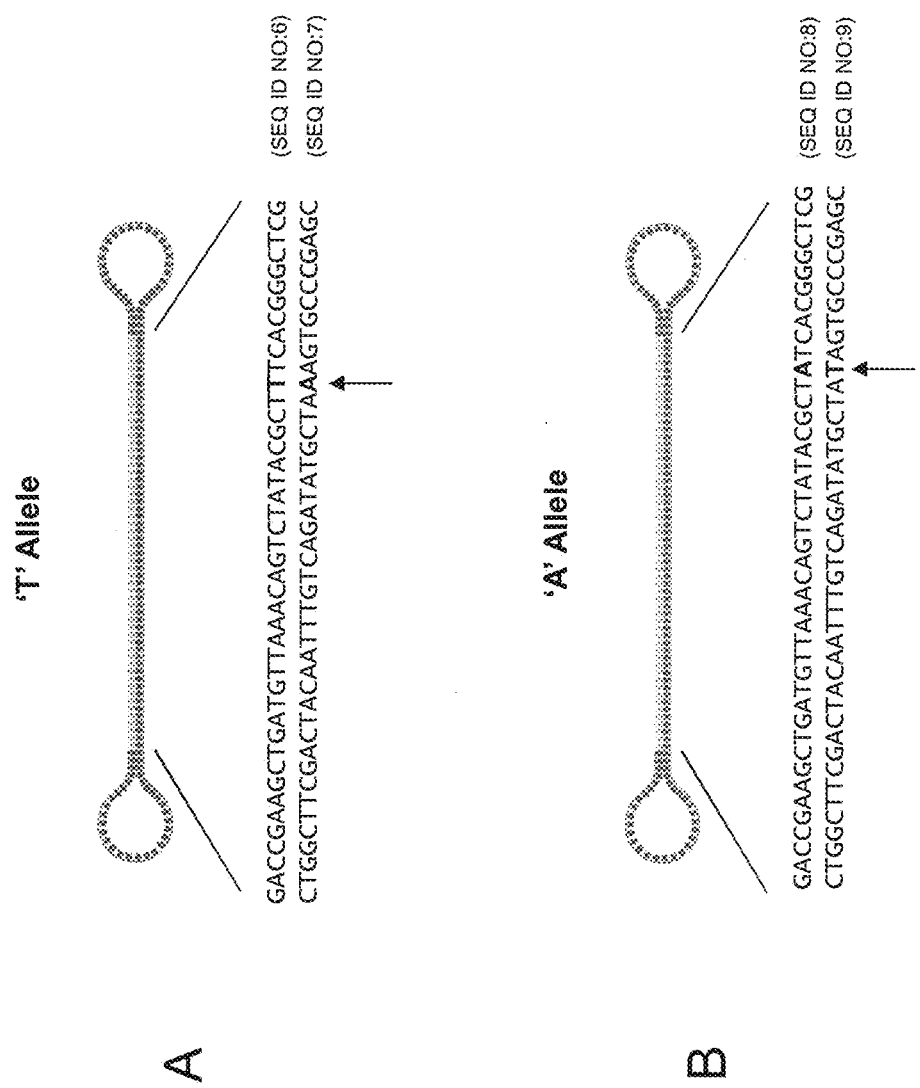
FIGS. 12A and 12B show a schematic illustration of single nucleotide variant template constructs.
Figure 13:
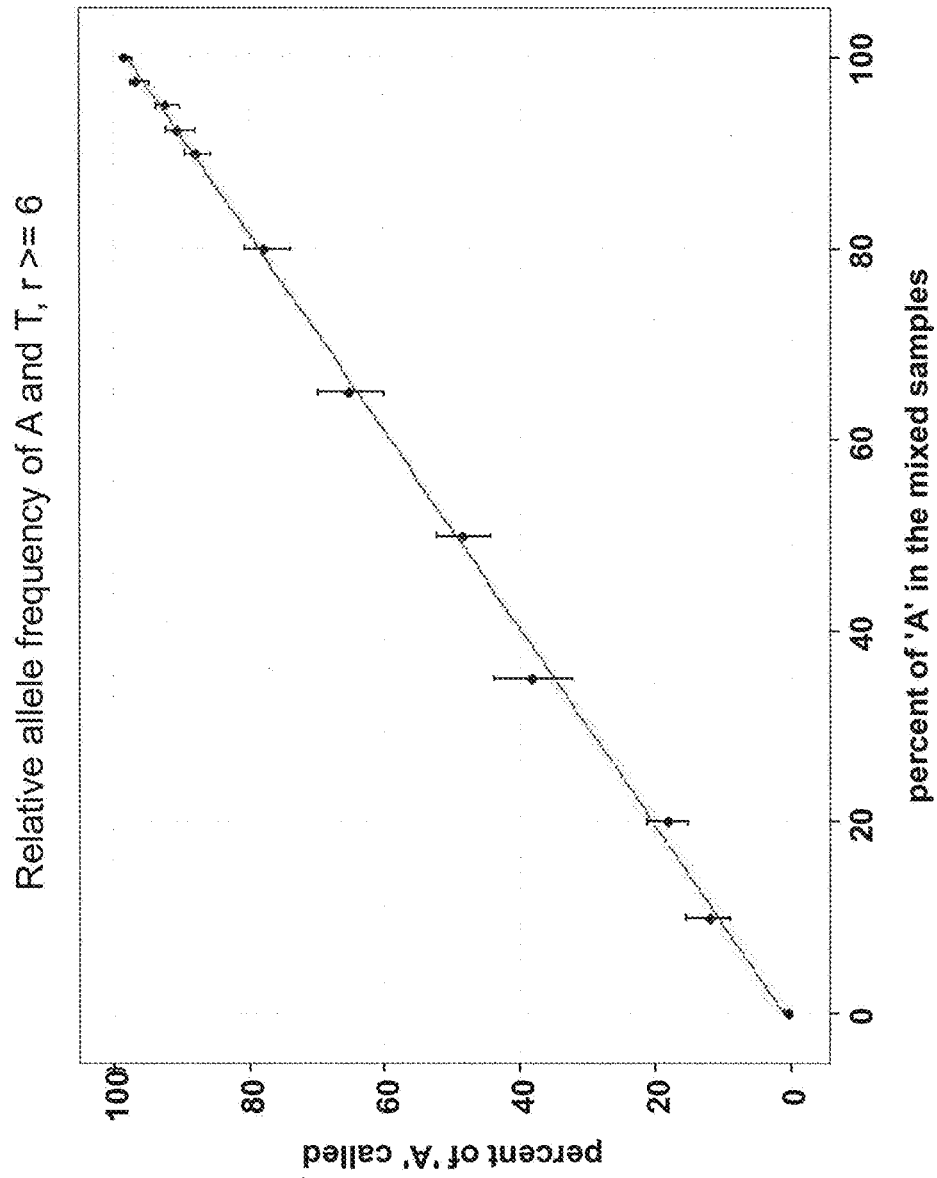
FIG. 13 shows a plot of the percentage of variant template in a reaction mixture vs. the percent of variants called experimentally.
Figure 14:
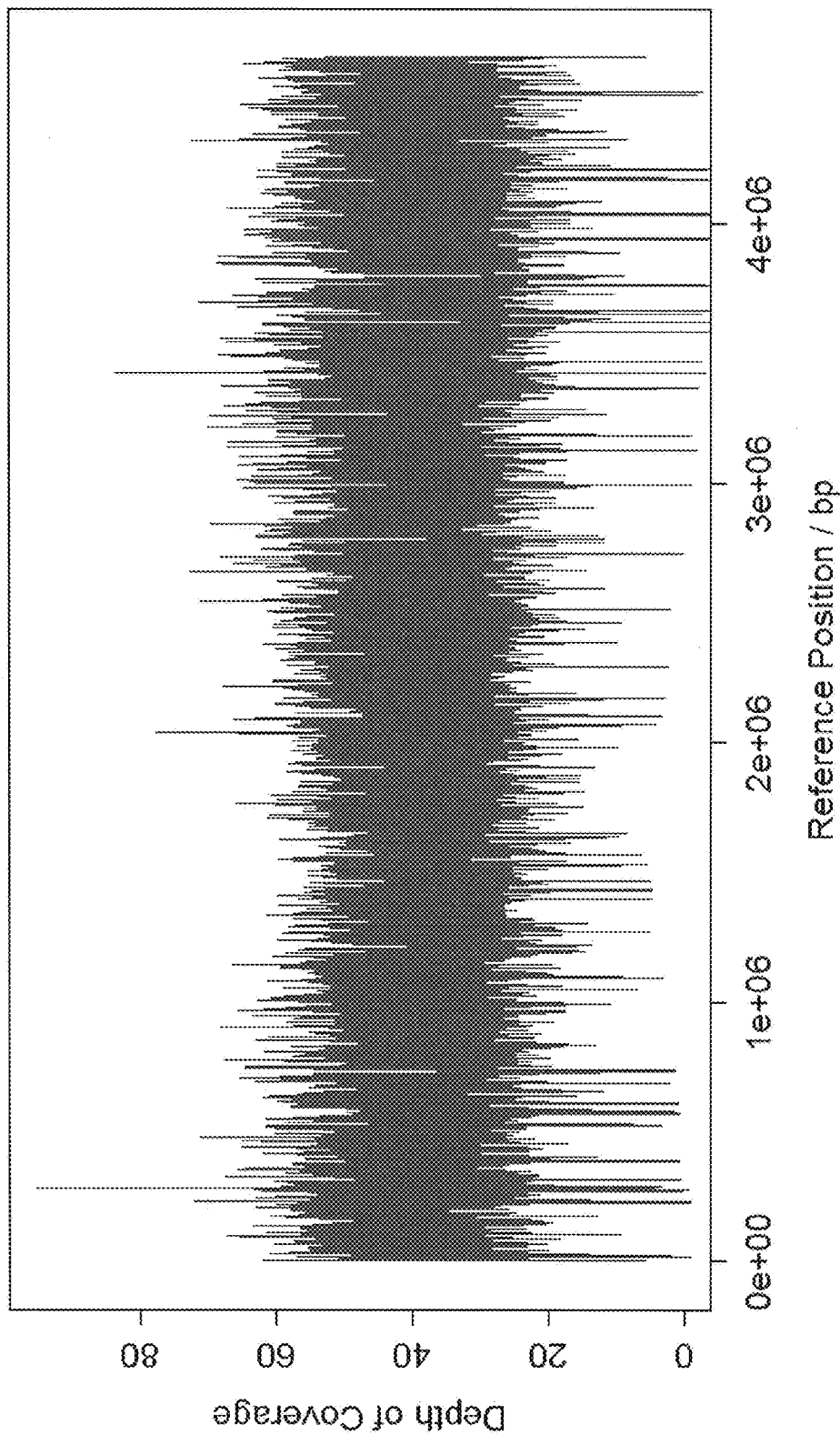
FIG. 14 shows a plot of sequence coverage over the entire *E. coli* genome, using the template constructs of the invention

This molecular redundant sequencing was applied in the identification of a single nucleotide variation, e.g., a SNP. Two SMRTbell™ templates were generated that differ at only a single nucleotide (indicated as the 'T' allele and the 'A' allele. The two templates are illustrated in FIG. 12, with the T allele shown in Panel A and marked at the variant base with the arrow, and the A allele shown in panel B. The two templates were mixed together at known ratios, ranging from 0% 'A':100% 'T' to 100% 'A':0% 'T'. Single molecule sequencing reactions were performed on each mixture. The resulting traces of sequencing data were filtered for those which contained 6 or greater reads of the insert sequence, and then used to generated consensus calls of the polymorphic position on individual molecules. FIG. 14 shows the comparison of the called polymorphism ratios to the expected ratios.

Example 3

Genomic E. coli Sequencing Using Contiguous Template Constructs

E. coli strain MG1655 was purchased from the ATCC and grown in LB media. DNA was harvested from the cell cultures using the High-molecular-weight genomic DNA purification kit from Qiagen. The genomic DNA was sheared using a nebulizer to generate fragments ranging from 500-1500 bp in size. Fragments were recovered using Qiagen PCR purification columns. The fragmented DNA was end repaired in a reaction containing T4 DNA polymerase, T4 polynucleotide kinase, and dNTPs. After purification, the end-repaired DNA was incubated in the presence of Taq DNA polymerase and dATP to add a single A nucleotide to each fragment. The tailed DNA was then ligated to hairpin oligos to generate the final SMRTbell™ templates. A single hairpin structure was used at both ends of the template. This hairpin contained a 54 nt single-stranded loop closed with an 8 bp stem, as well as a single T nucleotide at the 3' end to enable ligation to A-tailed insert fragments.

Fragments of sample material that failed to ligate with a hairpin at one or the other end, or that contained a nick due to incomplete ligation, were removed through the use of Exonuclease III and Exonuclease VII. The ligation products were concentrated by ethanol precipitation and then applied to a ChromSpin 1000 column to remove any templates that contained no insert or short inserts. The elution from the ChromaSpin column was purified using the Qiagen PCR purification columns and quantitated by absorbance at 260 nm. The templates were annealed to an equivalent amount of primer, and then subjected to sequencing.

Prior to immobilization on a ZMW array chip, 60 nM SMRTbell™ DNA Library was incubated at 37° C. for 1 hour with 10 nM modified Phi29 DNA polymerase (N62D, E375Y, K512Y, T368F) (see, e.g., U.S. Patent Application No. 61/072,645, filed Mar. 31, 2008, and incorporated herein by reference in its entirety for all purposes) bearing a biotinylation fusion protein tag, in the following buffer composition: 50 mM MOPS, pH 7.5, 75 mM Potassium Acetate, 0.05% Tween-20, 5 mM DTT, 500 nM ALEXA568-O-dG6P, 500 nM ALEXA555-O-dT6P, 500 nM ALEXA647-O-dA6P, 500 nM Cy5.5-O-dC6P, 1 mM Calcium Chloride. Just prior to immobilization, the mixture was diluted 10-fold in the same buffer composition and 8 µd was loaded onto the ZMW chip having surface immobilized streptavidin. The immobilization was carried out at room temperature for one hour. Prior to sequencing, the immobilization mixture was removed from the ZMW chip. The chip was washed 5 times with 8 µl of the following buffer: 50 mM ACES pH 7.1, 120 mM Potassium Acetate, 0.1 mM Calcium Chloride, 120 mM DTT. After these wash steps, 2 additional washes were performed with the following composition: 50 mM ACES pH 7.1, 120 mM Potassium Acetate, 0.1 mM Calcium Chloride, 250 nM ALEXA568-O-dG6P, 250 nM ALEXA555-O-dT6P, 250 nM ALEXA647-O-dA6P, 250 nM Cy5.5-O-dC6P, and 120 nM DTT. After the washes 4 µl of this nucleotide mix was left on the chip and the chip was placed in sequencing system as previously desribed. The reaction was initiated in real time as previously described by the addition of MnOAc to a final concentration of 0.5 mM.

Three 9 minute movies were taken for each ZMW chip for generating sequencing data as previously described. The sequenced fragments were aligned to the K12 MG1665 reference sequence.

Overall, the *E. coli* genome was sequenced to a depth of 38× coverage where 99.3% of the genome was unambiguously covered. Approximately 4.5 Mbp had relatively high coverage rates (i.e., greater than 20× coverage), giving approximately 99.99992% accuracy for a sequence accuracy score of Q61. For the entire genome, sequence accuracy was determined to be 99.9996%, equating to a quality score of approximately Q54.

Figure 15:
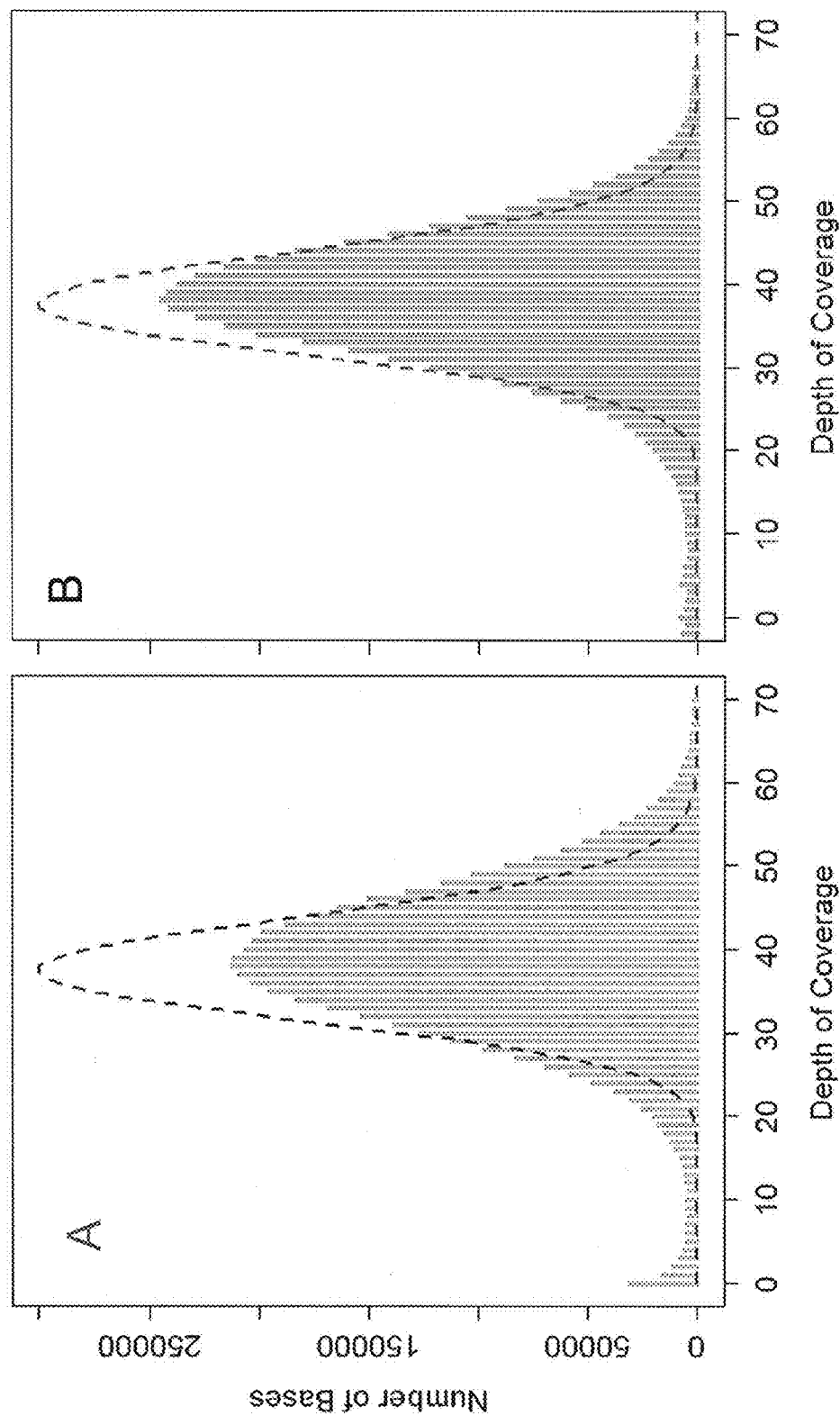
FIGS. 15A and 15B show plots of the number of bases vs. depth of coverage from *E. coli* genomic sequencing both uncorrected (FIG. 15A) and corrected (FIG. 15B) for the reduced replication of *E. coli* genome away from the origin of replication.

FIG. 14 illustrates the coverage map for the *E. coli* sequence. The plot was corrected for a known artifact related to reduced *E. coli* replication away from the origin of replication. As can be seen, the coverage level is highly uniform around the average level of 38× coverage. Plotted as a histogram of number of bases vs. level of coverage, the data show comparable distribution to the theoretical maximum coverage See FIG. 15, Panel A). Further, when corrected for the variation in replication away from the origin of replication, one can see that the actual observed sequence coverage (FIG. 15, Panel B, bars) begins to approach the theoretical maximum sequence coverage based upon Poisson statistics (shown by the dashed line).

Example 4

Large Insert Sequencing

Large repeated segments of genomic material are traditionally difficult to sequence and assemble into whole genomes since most sequencing platforms have readlength limitations (from tens of bases to hundreds of bases for pyrosequencing platforms and traditional capillary systems) that will not span these repeated regions, thus creating ambiguity in genomic assembly of sequence data, as to where a given sequence read may fit. Using SMRT™ sequencing and its substantially longer readlength, one is better able to span entire large repeat segments in individual reads, thus eliminating ambiguity faced by the shorter read systems.

Figure 16:
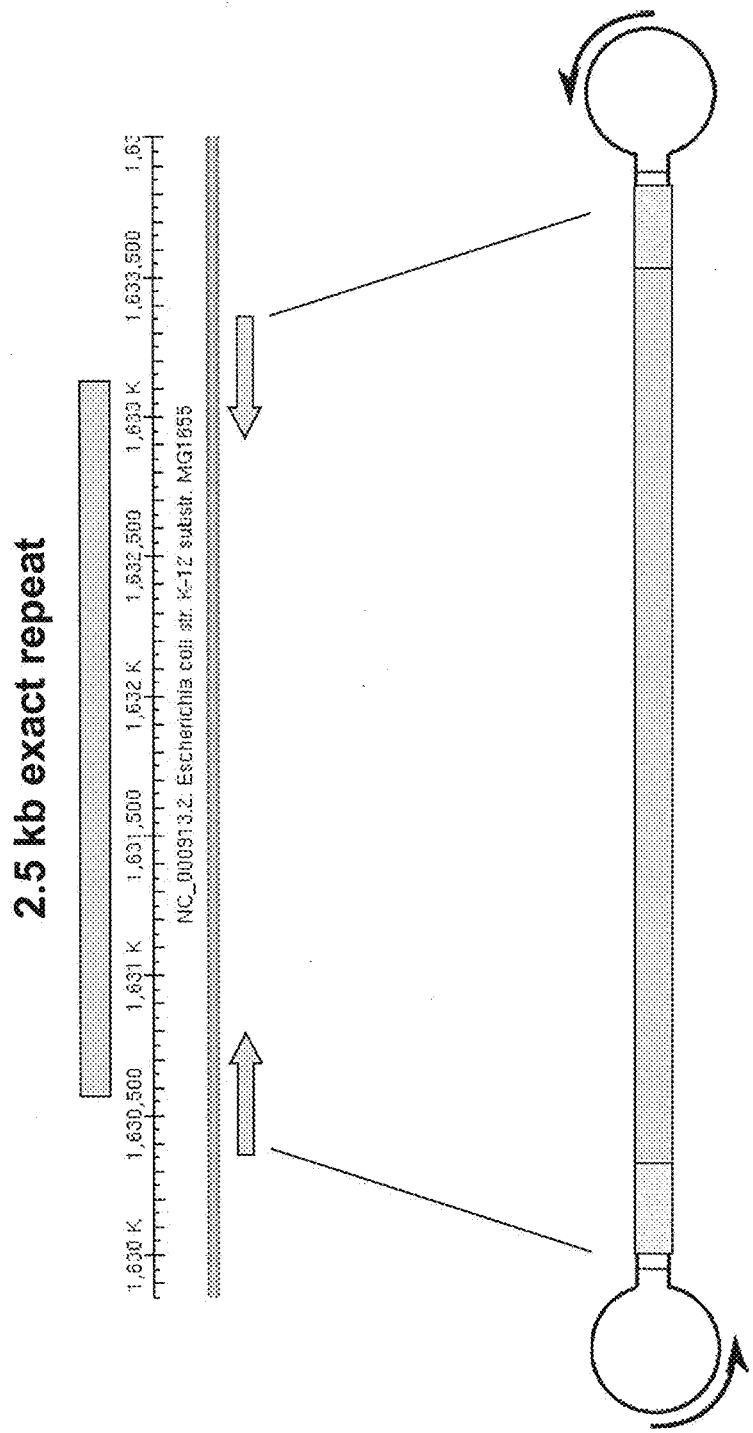
FIG. 16 shows a schematic illustration of a large repeat insert from *E. coli*, sequenced in a single contiguous template construct.

A portion of the genome sequence of *Escherichia coli* strain MG1655 that contains a 2.56 kb exact repeat was targeted for sequencing using the single molecule processes described herein. FIG. 16 provides a schematic illustration of the portion of the *E. coli* genome that includes this segment. The repeated segment is indicated as a grey bar over genome sequence. Primers targeting the sequence flanking this repeat region are indicated as arrows below the genome sequence. The resulting PCR product was phosphorylated using T4 DNA kinase, and then purified using Qiagen PCR purification columns. A single adenine nucleotide was added using Taq DNA polymerase in the presence of dATP, and then ligated to hairpin oligonucleotides using T4 DNA Ligase. Unligated material was removed using ExoIII and ExoVII. The SMRTbell™ template was concentrated by ethanol precipitation, passed through a ChromaSpin 1000 column, and then purified using Qiagen MinElute columns.

The template was then sequenced using a SMRT™ sequencing. Sequence reads were generated that spanned substantial portions, and in at least one case, the entire 3 kb segment (~3.2 kb read). By providing single sequence reads spanning the large insert, one significantly reduces any ambiguity that may be associated with such repeats.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method of obtaining a sequence of an individual double-stranded nucleic acid template molecule, the method comprising:
   (a) fragmenting a nucleic acid sample, thereby providing a plurality of double-stranded nucleic acid molecules, said double-stranded nucleic acid molecules comprising (i) a first strand, and (ii) a second strand, which is complementary to the first strand;
   (b) ligating a hairpin loop to a first end of said double-stranded nucleic acid molecules to covalently link said first strand and said second strand at said first end of said double-stranded nucleic acid molecules, thereby producing a plurality of double-stranded nucleic acid template molecules, wherein said first strand and said second strand at said first end of each of said plurality of double-stranded nucleic acid template molecules is linked by said hairpin loop;
   (c) identifying individual nucleotides of said first strand and said second strand of an individual double-stranded nucleic acid template molecule from said plurality of double-stranded nucleic acid template molecules produced in step (b) using a real time, single-molecule sequencing process, said single-molecule sequencing process consisting of sequencing said individual double-stranded nucleic acid template molecule, thereby generating a single sequencing read from said individual double-stranded nucleic acid template molecule, wherein said single sequencing read comprises a first nucleotide sequence of said first strand and a second nucleotide sequence of said second strand; and
   (d) obtaining a sequence of said individual double-stranded nucleic acid template molecule by analyzing said single sequencing read using both said first nucleotide sequence of said first strand and said second nucleotide sequence of said second strand, which includes comparing the first nucleotide sequence and the second nucleotide sequence from said individual double-stranded nucleic acid template molecule.

2. The method of claim 1, wherein said real time, single-molecule sequencing process comprises performing a polymerase mediated template directed sequencing process.

3. The method of claim 1, wherein said real time, single-molecule sequencing process is performed using an electrochemical system.

4. The method of claim 1, wherein said real time, single-molecule sequencing process is performed using a nanopore sensor.

5. The method of claim 1, wherein said plurality of double-stranded nucleic acid molecules comprise genomic DNA.

6. The method of claim 1, wherein said individual double-stranded nucleic acid template molecule comprises at least 500 base pairs.

7. The method of claim 1, wherein said hairpin loop comprises a registration sequence.

8. The method of claim 7, wherein said registration sequence is used for providing a basis for alignment of the first nucleotide sequence of the first strand to the second nucleotide sequence of the second strand.

9. The method of claim 1, wherein said hairpin loop comprises a barcode sequence.

10. The method of claim 1, wherein said individual double-stranded template molecule comprises a single-stranded segment.

11. The method of claim 10, wherein the single-stranded segment is an initiation point for the real-time, single molecule sequencing process.

* * * * *

SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: Primer for Amplification

<400> SEQUENCE: 1
gtacgggtct cacccgggga tcctctagaa tcgat       35

<210> SEQ ID NO 2
<211> LENGTH: 37
<212> TYPE: DNA
<213> ORGANISM: Artificial Sequence
<220> FEATURE:
<223> OTHER INFORMATION: Primer for Amplification

<400> SEQUENCE: 2
cctaaggtct cggaagctac tagtcctcag caagctt       37

<210> SEQ ID NO 3
<211> LENGTH: 24
<212> TYPE: DNA
<213> ORGANISM: Artificial Sequence
<220> FEATURE:

<223> OTHER INFORMATION: Hairpin oligo

<400> SEQUENCE: 3
cgggctcgga acgaaagttc cgag                                        24

<210> SEQ ID NO 4
<211> LENGTH: 74
<212> TYPE: DNA
<213> ORGANISM: Artificial Sequence
<220> FEATURE:
<223> OTHER INFORMATION: Hairpin oligo

<400> SEQUENCE: 4
cttcggtcgc cagattagaa aatcagtcac gtctagatgc agtcaggttc ttaaatccta    60
gttccttggc gacc                                                   74

<210> SEQ ID NO 5
<211> LENGTH: 24
<212> TYPE: DNA
<213> ORGANISM: Artificial Sequence
<220> FEATURE:
<223> OTHER INFORMATION: Sequencing primer

<400> SEQUENCE: 5
ctgactgcat ctagacgtga ctga                                        24

<210> SEQ ID NO 6
<211> LENGTH: 44
<212> TYPE: DNA
<213> ORGANISM: Artificial Sequence
<220> FEATURE:
<223> OTHER INFORMATION: Sequencing template

<400> SEQUENCE: 6
gaccgaagct gatgttaaac agtctatacg ctttcacggg ctcg                  44

<210> SEQ ID NO 7
<211> LENGTH: 44
<212> TYPE: DNA
<213> ORGANISM: Artificial Sequence
<220> FEATURE:
<223> OTHER INFORMATION: Sequencing template

<400> SEQUENCE: 7
cgagcccgtg aaatcgtata gactgtttaa catcagcttc ggtc                  44

<210> SEQ ID NO 8
<211> LENGTH: 44
<212> TYPE: DNA
<213> ORGANISM: Artificial Sequence
<220> FEATURE:
<223> OTHER INFORMATION: Sequencing template

<400> SEQUENCE: 8
gaccgaagct gatgttaaac agtctatacg ctatcacggg ctcg                  44

<210> SEQ ID NO 9
<211> LENGTH: 44
<212> TYPE: DNA
<213> ORGANISM: Artificial Sequence

```
<220> FEATURE:
<223> OTHER INFORMATION: Sequencing template

<400> SEQUENCE: 9
cgagcccgtg atatcgtata gactgtttaa catcagcttc ggtc            44
```